US009517357B2

(12) United States Patent
Omenetto et al.

(10) Patent No.: US 9,517,357 B2
(45) Date of Patent: Dec. 13, 2016

(54) PLASMONIC NANOPARTICLE-DOPED SILK MATERIALS

(75) Inventors: Fiorenzo Omenetto, Lexington, MA (US); David L. Kaplan, Concord, MA (US); Hu Tao, Medford, MA (US)

(73) Assignee: TUFTS UNIVERSITY, Medford, MA (US)

( * ) Notice: Subject to any disclaimer, the term of this patent is extended or adjusted under 35 U.S.C. 154(b) by 955 days.

(21) Appl. No.: 13/819,419

(22) PCT Filed: Sep. 3, 2011

(86) PCT No.: PCT/US2011/050453
§ 371 (c)(1),
(2), (4) Date: Aug. 7, 2013

(87) PCT Pub. No.: WO2012/031282
PCT Pub. Date: Mar. 8, 2012

(65) Prior Publication Data
US 2013/0310908 A1    Nov. 21, 2013

Related U.S. Application Data

(60) Provisional application No. 61/379,905, filed on Sep. 3, 2010.

(51) Int. Cl.
*A61N 5/00* (2006.01)
*A61N 5/06* (2006.01)
(Continued)

(52) U.S. Cl.
CPC .............. *A61N 5/0625* (2013.01); *A61F 7/03* (2013.01); *A61L 31/005* (2013.01); *A61L 31/125* (2013.01);
(Continued)

(58) Field of Classification Search
CPC ........ A61L 31/00; A61L 31/12; A61L 31/125; A61L 31/14; A61N 5/062; A61N 5/0625
See application file for complete search history.

(56) References Cited

U.S. PATENT DOCUMENTS 5,245,012 A    9/1993   Lombari et al.
6,131,581 A   10/2000   Leysieffer et al.
(Continued)

FOREIGN PATENT DOCUMENTS

CN         1813645 A    8/2006
CN       101406713 A    4/2009
(Continued)

OTHER PUBLICATIONS

Amsden, J.J. et al., Rapid Nanoimprinting of Silk Fibroin Films for Biophotonic Applications, Advanced Materials, 22(15):1746-1749 (2010).
(Continued)

*Primary Examiner* — Kaitlyn Smith
(74) *Attorney, Agent, or Firm* — Choate, Hall & Stewart, LLP

(57) ABSTRACT

Provided herein are silk fibroin-based photothermal elements and uses thereof. The silk fibroin-based photothermal elements comprise a plurality of plasmonic nanoparticle distributed in a silk fibroin matrix, and can generate heat when the plasmonic nanoparticles are exposed to electromagnetic radiation. The silk fibroin-based photothermal elements can be adapted to be conformable and biodegradable, and can further be integrated with various electronic components, such as a thermo-electric device for conversion of heat into electricity. The invention is useful for various in vivo applications, such as photothermal therapy, controlled drug-delivery devices or wireless powering of implanted micro-devices.

31 Claims, 3 Drawing Sheets

(51) Int. Cl.
*A61F 7/03* (2006.01)
*A61L 31/00* (2006.01)
*A61L 31/12* (2006.01)
*A61L 31/14* (2006.01)
*H01L 35/30* (2006.01)

(52) U.S. Cl.
CPC .............. *A61L 31/14* (2013.01); *A61N 5/062* (2013.01); *H01L 35/30* (2013.01); *A61L 2400/12* (2013.01); *Y10T 428/268* (2015.01); *Y10T 428/2927* (2015.01)

(56) References Cited

U.S. PATENT DOCUMENTS

| | | | |
|---|---|---|---|
| 6,287,340 B1 | 9/2001 | Altman et al. | |
| 6,428,811 B1 | 8/2002 | West et al. | |
| 6,530,944 B2 | 3/2003 | West et al. | |
| 6,685,730 B2 | 2/2004 | West et al. | |
| 6,902,932 B2 | 6/2005 | Altman et al. | |
| 7,532,937 B2 | 5/2009 | Horio et al. | |
| 7,635,755 B2 | 12/2009 | Kaplan et al. | |
| 7,727,542 B2 | 6/2010 | DiBenedetto et al. | |
| 8,206,774 B2 | 6/2012 | Kaplan et al. | |
| 8,293,486 B2 * | 10/2012 | Kaplan ............ | A61K 47/48246 435/7.1 |
| 8,501,172 B2 | 8/2013 | Kaplan et al. | |
| 8,666,471 B2 | 3/2014 | Rogers et al. | |
| 2003/0093092 A1 | 5/2003 | West et al. | |
| 2007/0212730 A1 | 9/2007 | Vepari et al. | |
| 2008/0199510 A1 | 8/2008 | Ruane et al. | |
| 2009/0171404 A1 | 7/2009 | Irani et al. | |
| 2010/0065784 A1 | 3/2010 | Kaplan et al. | |
| 2011/0202125 A1 | 8/2011 | Luo et al. | |
| 2012/0129255 A1* | 5/2012 | Kaplan ............ | A61K 47/48246 435/375 |
| 2014/0145365 A1* | 5/2014 | Omenetto ............... | H01L 21/02 264/104 |
| 2014/0334005 A1* | 11/2014 | Omenetto .......... | B29D 11/0074 359/577 |

FOREIGN PATENT DOCUMENTS

| | | |
|---|---|---|
| JP | 2009-529975 A | 8/2009 |
| WO | WO-97/08315 A1 | 3/1997 |
| WO | WO-03/056297 A2 | 7/2003 |
| WO | WO-04/001103 A2 | 12/2003 |
| WO | WO-2004/000915 A2 | 12/2003 |
| WO | WO-2004/062697 A2 | 7/2004 |
| WO | WO-2005/000483 A1 | 1/2005 |
| WO | WO-2005/012606 A2 | 2/2005 |
| WO | WO-2005/123114 A2 | 12/2005 |
| WO | WO-2006/042287 A2 | 4/2006 |
| WO | WO-2006/076711 A2 | 7/2006 |
| WO | WO-2007/016524 A2 | 2/2007 |
| WO | WO-2007/103442 A1 | 9/2007 |
| WO | WO-2008085904 A1 | 7/2008 |
| WO | WO-2008/106485 A2 | 9/2008 |
| WO | WO-2008/108838 A2 | 9/2008 |
| WO | WO-2008/118133 A2 | 10/2008 |
| WO | WO-2008/118211 A2 | 10/2008 |
| WO | WO-2008/127401 A2 | 10/2008 |
| WO | WO-2008/127402 A2 | 10/2008 |
| WO | WO-2008/127403 A2 | 10/2008 |
| WO | WO-2008/127404 A2 | 10/2008 |
| WO | WO-2008/127405 A2 | 10/2008 |
| WO | WO-2008/140562 A2 | 11/2008 |
| WO | WO-2008/150861 A1 | 12/2008 |
| WO | WO-2009/061823 A1 | 5/2009 |
| WO | WO-2009/100280 A2 | 8/2009 |
| WO | WO-2009/105537 A2 | 8/2009 |
| WO | WO-2009/126689 A2 | 10/2009 |
| WO | WO-2009/140588 A1 | 11/2009 |
| WO | WO-2010/036992 A2 | 4/2010 |
| WO | WO-2010/042798 A2 | 4/2010 |
| WO | WO-2010/057142 A2 | 5/2010 |
| WO | WO-2010/065957 A2 | 6/2010 |
| WO | WO-2010/126640 A2 | 11/2010 |
| WO | WO-2010/141133 | 12/2010 |
| WO | WO-2011/005381 A2 | 1/2011 |
| WO | WO-2011/006133 A2 | 1/2011 |
| WO | WO-2011/008842 A2 | 1/2011 |
| WO | WO-2011/011347 A2 | 1/2011 |
| WO | WO-2011/026101 A2 | 3/2011 |
| WO | WO-2011/038401 A2 | 3/2011 |
| WO | WO-2011/041395 A2 | 4/2011 |
| WO | WO-2011/046652 A2 | 4/2011 |
| WO | WO-2011/115643 A1 | 9/2011 |
| WO | WO-2011130335 A2 | 10/2011 |
| WO | WO-2012/031282 A2 | 3/2012 |

OTHER PUBLICATIONS

Amsden, J.J. et al., Spectral analysis of induced color change on periodically nanopatterned silk films, Opt. Express, 17(23):21271-9 (2009).

Baciu, C.L. et al., Protein-membrane interaction probed by single plasmonic nanoparticles, Nano. Lett., 8(6):1724-8 (2008).

Bini, E. et al., Mapping domain structures in silks from insects and spiders related to protein assembly, Journal of Molecular Biology, 335(1):27-40 (2004).

Cobley, C.M. et al., Targeting gold nanocages to cancer cells for photothermal destruction and drug delivery, Expert Opin. Drug Deliv., 7(5):577-87 (2010).

Disalvo, F.J., Thermoelectric cooling and power generation, Science, 285(5428):703-6 (1999).

Dong et al., Biogenic synthesis of hierarchical hybrid nanocomposites and patterning of silver nanoparticles, Mats. Chem. Phys., 110:160 (2008).

Elman, N.M., et al., An implantable MEMS drug delivery device for rapid delivery in ambulatory emergency care, Biomed. Microdevices, 11(3):625-31 (2009).

Fotopoulou, K. and Flynn, B.W., Wireless Powering of Implanted Sensors using RF Inductive Coupling, 2006 5th IEEE Conf. Sensors, EXCO, Daegu, Korea, 765-768 (2007).

Glatz et al., Bi2Te3-based flexible micro thermoelectric generator with optimized design, J. Microelectromechanical Sys., 18(3):763-772 (2009).

Glatz et al., Optimization and fabrication of thick flexible polymer based micro thermoelectric generator, Sensors and Actuators A., 132 :337 (2006).

Gupta, et al., Fabrication and Characterization of Silk Fibroin-derived Curcumin Nanoparticles for Cancer Therapy, International Journal for Nanomedicine, 4:115-122 (2009).

Hamblin, M.R. And Demidova, T.N., Mechanisms of low level light therapy, Proc. SPIE 6140, Mechanisms for Low-Light Therapy, 614001 (Feb. 10, 2006).

Hilt, J.Z. and Peppas, N.A., Microfabricated drug delivery devices, Int. J. Pharm., 306(1-2):15-23 (2005).

Hirsch, L.R. et al., Nanoshell-mediated near-infrared thermal therapy of tumors under magnetic resonance guidance, Proc. Natl. Acad. Sci. U S A., 100(23):13549-54 (2003).

Hsia, T.Y. et al., Novel minimally invasive, intrapericardial implantable cardioverter defibrillator coil system: a useful approach to arrhythmia therapy in children, Ann. Thorac. Surg., 87(4):1234-8 (2009).

Jaeger, G.T. et al., Two years follow-up study of the pain-relieving effect of gold bead implantation in dogs with hip-joint arthritis, Acta Vet. Scand., 49:9 (2007).

Jaremko, J. and Rorstad, O., Advances toward the implantable artificial pancreas for treatment of diabetes, Diabetes Care., 21(3):444-50 (1998).

Jin, H. et al., Water-Stable Silk Films with Reduced β-Sheet Content, Advanced Functional Materials, 15:241-1247 (2005).

Jin, H.J. and Kaplan, D.L., Mechanism of silk processing in insects and spiders, Nature, 424(6952):1057-1061 (2003).

(56) References Cited

OTHER PUBLICATIONS

Kharlampieva, E. et al., Silk-based Mechanically-robust Ultrathin Nano-composites with Tailored Optical Properties, Polymeric Materials: Science and Engineering, 101:1059 (2009).

Kikuchi, Y. et al., Structure of the Bombyx mori fibroin light-chain-encoding gene: upstream sequence elements common to the light and heavy chain, Gene, 110(2):151-8 (1992).

Kim et al. Silicon Electronics on Silk as a Path to Bioresorbable, Implantable Devices, Appl. Phys. Lett. 95:133701-133703 (2009).

Kim, D.H. et al., Dissolvable films of silk fibroin for ultrathin conformal bio-integrated electronics, Nat. Mater., 9(6):511-517 (2010).

Kim, H. et al., Finite Element Analysis of a Thin-Film Thermoelectric Module for Thermal Management in Micro Electronics, PowerMEMS 2009, pp. 281-284 (Washington, DC, Dec. 1-4, 2009).

Kim, U-J. et al., Structure and Properties of Silk Hydrogels, Biomacromol., 5:786-792 (2004).

Krishnan, S. et al., Nanoparticle-mediated thermal therapy: evolving strategies for prostate cancer therapy, Int. J. Hyperthermia., 26(8):775-89 (2010).

Lawrence, B.D. et al., Bioactive silk protein biomaterial systems for optical devices, Biomacromolecules, 9:1214-1220 (2008).

Lu, Q. et al., Stabilization and release of enzymes from silk films, Macromol. Biosci., 10(4):359-68 (2010).

Lu, X. et al., Chemical synthesis of novel plasmonic nanoparticles, Annu. Rev. Phys. Chem., 60:167-92 (2009).

Lu, Y. and Chen, S.C., Micro and nano-fabrication of biodegradable polymers for drug delivery, Adv. Drug. Deliv. Rev., 56(11):1621-33 (2004).

Lucas F. et al., The silk fibroins, Advances in Protein Chemistry, 13:107-242 (1958).

Maisel, W.H. and Kohno, T., Improving the security and privacy of implantable medical devices, N. Engl. J. Med., 362(13):1164-6 (2010).

McAlister, F.A. et al., Cardiac resynchronization therapy and implantable cardiac defibrillators in left ventricular systolic dysfunction, Evid. Rep. Technol. Assess. (Full Rep)., (152):1-199 (2007).

Mobbs, R.J. et al., Peripheral nerve stimulation for the treatment of chronic pain, J. Clin. Neurosci., 14(3):216-21; discussion 222-3 (2007).

Narazaki, G. and Yamashita, J.K., Creations of biological Pacemaker, Inflammation and Regeneration, 29(2):123-127 (2009).

Nazarov, R. et al., Porous 3-D scaffolds from regenerated silk fibroin, Biomacromolecules, 5(3):718-26 (2004).

O'Neal, D.P. et al., Photo-thermal tumor ablation in mice using near infrared-absorbing nanoparticles, Cancer Lett., 209:171-176 (2009).

Omenetto, F. and Kaplan, D., A new route for silk, Nature Photonics, 2:641-643 (2008).

Omenetto, F.G. and Kaplan, D.L., New Opportunities for an Ancient Material, Science, 329:528-531 (2010).

Parker et al., Biocompatible Silk Printed Optical Waveguides, Adv. Mater., 21:2411-2415 (2009).

Prodan, E. et al., Electronic Structure and Optical Properties of Gold Nanoshells, Nano Letters, 3(10):1411-1415 (2003).

Singh et al., Advances in the Treatment of Parkinson's Disease, 81 Progress in Neurobiology 29-44 (2007).

Soma, M. et al., Radio-frequency coils in implantable devices: misalignment analysis and design procedure, IEEE Trans. Biomed. Eng., 34(4):276-82 (1987).

Staples, M. et al., Application of micro- and nano-electromechanical devices to drug delivery, Pharm. Res., 23(5):847-63 (2006).

Stolik, S. et al., Measurement of the penetration depths of red and near infrared light in human "ex vivo" tissues, J. Photochem. Photobiol. B., 57(2-3):90-3 (2000).

Svaasand, L.O. et al., On the Physical Rationale of Laser Induced Hyperthermia, Lasers Med. Sci., 5:121-128 (1990).

Takei, F. et al., Further evidence for importance of the subunit combination of silk fibroin in its efficient secretion from the posterior silk gland cells, Journal of Cellular Biology, 105(1):175-180 (1987).

Takeuchi, S. and Shimoyama, I., Selective drive of electrostatic actuators using remote inductive powering, Sens. Actuators, A 95:269-273 (2002).

Tanaka, K. et al., Determination of the site of disulfide linkage between heavy and light chains of silk fibroin produced by Bombyx mori, Biochimica et Biophysica Acta, 1432:92-103 (1999).

Tanaka, K. et al., Immunological identification of the major disulfide-linked light component of silk fibroin, Journal of Biochemistry, 114(1):1-4 (1993).

Valluzzi, R., et al., Orientation of silk III at the air-water interface, Int. J. Biol. Macromol., 24(2-3): 237-242 (1999).

Ye, J. et al., Fabrication and Optical Properties of Gold Semishells, J. Phys.Chem. C, 113:3110-3115 (2009).

Ye, J. et al., Fabrication, characterization, and optical properties of gold nanobowl submonolayer structures, Langmuir, 25(3):1822-7 (2009).

Ye, J. et al., Plasmonic modes of metallic semishells in a polymer film, ACS Nano., 4(3):1457-64 (2010).

Ye, J. et al., Symmetry breaking induced optical properties of gold open shell nanostructures, Opt. Express, 17(26):23765-71 (2009).

Zhang, Y-Q et al., Formation of silk fibroin nanoparticles in water-miscible organic solvent and their characterization, Journal of Nanoparticle Research, 9:885-900 (2007).

Zhou, C.Z. et al, Fine organization of Bombyx mori fibroin heavy chain gene, Nucleic Acids Research, 28(12):2413-2419 (2000).

International Preliminary Report on Patentability of PCT/US2011/050453, 8 pages (Mar. 14, 2013).

International Search Report of PCT/US2011/050453, 6 pages (Apr. 24, 2012).

Written Opinion of PCT/US2011/050453, 6 pages (Apr. 24, 2012).

* cited by examiner

SEQUENCE LISTING

```
<160> NUMBER OF SEQ ID NOS: 22

<210> SEQ ID NO 1
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (7)..(90)
<223> OTHER INFORMATION: Wherein any of residues 7-90 may be missing.

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser
                85                  90
```

```
<210> SEQ ID NO 2
<211> LENGTH: 30
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is V, I or A.
<220> FEATURE:
<221> NAME/KEY: MISC_FEATURE
<222> LOCATION: (3)..(30)
<223> OTHER INFORMATION: Wherein any of residues 3-30 may be missing
<220> FEATURE:
<221> NAME/KEY: MISC_FEATURE
<222> LOCATION: (4)..(4)
<223> OTHER INFORMATION: Wherein X is V, I or A.
<220> FEATURE:
<221> NAME/KEY: MISC_FEATURE
<222> LOCATION: (6)..(6)
<223> OTHER INFORMATION: Wherein X is V, I or A.
<220> FEATURE:
<221> NAME/KEY: MISC_FEATURE
<222> LOCATION: (8)..(8)
<223> OTHER INFORMATION: Wherein X is V, I or A.
<220> FEATURE:
<221> NAME/KEY: MISC_FEATURE
<222> LOCATION: (10)..(10)
<223> OTHER INFORMATION: Wherein X is V, I or A.
<220> FEATURE:
<221> NAME/KEY: MISC_FEATURE
<222> LOCATION: (12)..(12)
<223> OTHER INFORMATION: Wherein X is V, I or A.
<220> FEATURE:
<221> NAME/KEY: MISC_FEATURE
<222> LOCATION: (14)..(14)
<223> OTHER INFORMATION: Wherein X is V, I or A.
<220> FEATURE:
<221> NAME/KEY: MISC_FEATURE
<222> LOCATION: (16)..(16)
<223> OTHER INFORMATION: Wherein X is V, I or A.
<220> FEATURE:
<221> NAME/KEY: MISC_FEATURE
<222> LOCATION: (18)..(18)
<223> OTHER INFORMATION: Wherein X is V, I or A.
<220> FEATURE:
<221> NAME/KEY: MISC_FEATURE
<222> LOCATION: (20)..(20)
<223> OTHER INFORMATION: Wherein X is V, I or A.
<220> FEATURE:
<221> NAME/KEY: MISC_FEATURE
<222> LOCATION: (22)..(22)
<223> OTHER INFORMATION: Wherein X is V, I or A.
<220> FEATURE:
<221> NAME/KEY: MISC_FEATURE
<222> LOCATION: (24)..(24)
<223> OTHER INFORMATION: Wherein X is V, I or A.
<220> FEATURE:
<221> NAME/KEY: MISC_FEATURE
<222> LOCATION: (26)..(26)
<223> OTHER INFORMATION: Wherein X is V, I or A.
<220> FEATURE:
<221> NAME/KEY: MISC_FEATURE
<222> LOCATION: (28)..(28)
<223> OTHER INFORMATION: Wherein X is V, I or A.
<220> FEATURE:
<221> NAME/KEY: MISC_FEATURE
<222> LOCATION: (30)..(30)
<223> OTHER INFORMATION: Wherein X is V, I or A.

<400> SEQUENCE: 2

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa
            20                  25                  30
```

-continued

```
<210> SEQ ID NO 3
<211> LENGTH: 4
<212> TYPE: PRT
<213> ORGANISM: Bombyx mori

<400> SEQUENCE: 3

Gly Ala Ala Ser
1

<210> SEQ ID NO 4
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (14)..(15)
<223> OTHER INFORMATION: Wherein any of residues 14-15 may be missing

<400> SEQUENCE: 4

Ser Ser Ala Ala Ala Ala Ala Ala Ala Ala Ala Ala Ala Ala Ala
1               5                   10                  15

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(5)
<223> OTHER INFORMATION: Wherein any of residues 2-5 may be missing
<220> FEATURE:
<221> NAME/KEY: MISC_FEATURE
<222> LOCATION: (2)..(2)
<223> OTHER INFORMATION: Wherein X is any residue
<220> FEATURE:
<221> NAME/KEY: MISC_FEATURE
<222> LOCATION: (3)..(3)
<223> OTHER INFORMATION: Wherein X is any residue
<220> FEATURE:
<221> NAME/KEY: MISC_FEATURE
<222> LOCATION: (4)..(4)
<223> OTHER INFORMATION: Wherein X is any residue
<220> FEATURE:
<221> NAME/KEY: MISC_FEATURE
<222> LOCATION: (5)..(5)
<223> OTHER INFORMATION: Wherein X is any residue
<220> FEATURE:
<221> NAME/KEY: MISC_FEATURE
<222> LOCATION: (8)..(8)
<223> OTHER INFORMATION: Wherein X is any residue

<400> SEQUENCE: 5

Gly Xaa Xaa Xaa Xaa Gly Gly Xaa
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is A, S, Y, R, D, V or W
```

```
<400> SEQUENCE: 6

Gly Gly Gly Xaa
1

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (4)..(6)
<223> OTHER INFORMATION: Wherein any residues 4-6 may be missing

<400> SEQUENCE: 7

Ser Ser Ala Ala Ala Ala Ser Ser Ala Ala Ala Ala
1               5                   10

<210> SEQ ID NO 8
<211> LENGTH: 6
<212> TYPE: PRT
<213> ORGANISM: Galleria mellonella

<400> SEQUENCE: 8

Gly Leu Gly Gly Leu Gly
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is L, I, V or P
<220> FEATURE:
<221> NAME/KEY: MISC_FEATURE
<222> LOCATION: (5)..(5)
<223> OTHER INFORMATION: Wherein X is L, I, V or P

<400> SEQUENCE: 9

Gly Xaa Gly Gly Xaa Gly
1               5

<210> SEQ ID NO 10
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Wherein X is Y, V, S or A
<220> FEATURE:
<221> NAME/KEY: MISC_FEATURE
<222> LOCATION: (6)..(20)
<223> OTHER INFORMATION: Wherein any of 6-20 may be missing
<220> FEATURE:
<221> NAME/KEY: MISC_FEATURE
<222> LOCATION: (10)..(10)
<223> OTHER INFORMATION: Wherein X is Y, V, S or A
```

```
<220> FEATURE:
<221> NAME/KEY: MISC_FEATURE
<222> LOCATION: (15)..(15)
<223> OTHER INFORMATION: Wherein X is Y, V, S or A
<220> FEATURE:
<221> NAME/KEY: MISC_FEATURE
<222> LOCATION: (20)..(20)
<223> OTHER INFORMATION: Wherein X is Y, V, S or A

<400> SEQUENCE: 10

Gly Pro Gly Gly Xaa Gly Pro Gly Gly Xaa Gly Pro Gly Gly Xaa Gly
1               5                   10                  15

Pro Gly Gly Xaa Tyr
            20

<210> SEQ ID NO 11
<211> LENGTH: 5
<212> TYPE: PRT
<213> ORGANISM: Argiope trifasciata

<400> SEQUENCE: 11

Gly Arg Gly Gly Ala
1               5

<210> SEQ ID NO 12
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(10)
<223> OTHER INFORMATION: Wherein any of 5-10 may be missing

<400> SEQUENCE: 12

Gly Ala Gly Ala Ala Ala Ala Ala Ala Ala Gly Gly Ala
1               5                   10

<210> SEQ ID NO 13
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Wherein X is Q, Y, L, A, S or R
<220> FEATURE:
<221> NAME/KEY: MISC_FEATURE
<222> LOCATION: (5)..(5)
<223> OTHER INFORMATION: Wherein X is Q, Y, L, A, S or R
<220> FEATURE:
<221> NAME/KEY: MISC_FEATURE
<222> LOCATION: (7)..(7)
<223> OTHER INFORMATION: Wherein X is Q, Y, L, A, S or R
<220> FEATURE:
<221> NAME/KEY: MISC_FEATURE
<222> LOCATION: (8)..(8)
<223> OTHER INFORMATION: Wherein X is Q, Y, L, A, S or R

<400> SEQUENCE: 13

Gly Gly Xaa Gly Xaa Gly Xaa Xaa
1               5

<210> SEQ ID NO 14
<211> LENGTH: 16
<212> TYPE: PRT
<213> ORGANISM: Bombyx mori
```

```
<400> SEQUENCE: 14

Thr Gly Ser Ser Gly Phe Gly Pro Tyr Val Asn Gly Gly Tyr Ser Gly
1               5                   10                  15

<210> SEQ ID NO 15
<211> LENGTH: 8
<212> TYPE: PRT
<213> ORGANISM: Bombyx mandarina

<400> SEQUENCE: 15

Tyr Glu Tyr Ala Trp Ser Ser Glu
1               5

<210> SEQ ID NO 16
<211> LENGTH: 7
<212> TYPE: PRT
<213> ORGANISM: Antheraea mylitta

<400> SEQUENCE: 16

Ser Asp Phe Gly Thr Gly Ser
1               5

<210> SEQ ID NO 17
<211> LENGTH: 7
<212> TYPE: PRT
<213> ORGANISM: Antheraea yamamai

<400> SEQUENCE: 17

Arg Arg Ala Gly Tyr Asp Arg
1               5

<210> SEQ ID NO 18
<211> LENGTH: 8
<212> TYPE: PRT
<213> ORGANISM: Galleria mellonella

<400> SEQUENCE: 18

Glu Val Ile Val Ile Asp Asp Arg
1               5

<210> SEQ ID NO 19
<211> LENGTH: 18
<212> TYPE: PRT
<213> ORGANISM: Nephila madascariensis

<400> SEQUENCE: 19

Thr Thr Ile Ile Glu Asp Leu Asp Ile Thr Ile Asp Gly Ala Asp Gly
1               5                   10                  15

Pro Ile

<210> SEQ ID NO 20
<211> LENGTH: 8
<212> TYPE: PRT
<213> ORGANISM: Nephila clavipes

<400> SEQUENCE: 20

Thr Ile Ser Glu Glu Leu Thr Ile
1               5

<210> SEQ ID NO 21
<211> LENGTH: 6
<212> TYPE: PRT
<213> ORGANISM: Artificial sequence
```

```
-continued

<220> FEATURE:
<223> OTHER INFORMATION: Synthetic polypeptide

<400> SEQUENCE: 21

Gly Ser Gly Ala Gly Ala
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is any residue
<220> FEATURE:
<221> NAME/KEY: MISC_FEATURE
<222> LOCATION: (5)..(5)
<223> OTHER INFORMATION: Wherein X is any residue

<400> SEQUENCE: 22

Gly Pro Gly Xaa Xaa
1               5
```

PLASMONIC NANOPARTICLE-DOPED SILK MATERIALS

RELATED APPLICATIONS

This application is a 35 U.S.C. §371 National Stage of International Application No. PCT/US2011/050453, entitled "Plasmonic Nanoparticle-Doped Silk Materials" filed Sep. 3, 2011, which claims the benefit of and priority to U.S. Provisional Application No. 61/379,905 filed Sep. 3, 2010, the entire contents of which are hereby incorporated by reference.

GOVERNMENT SUPPORT

This invention was made with government support under grant W911NF-07-1-0618 awarded by the United States Army Research Office and grant FA9550-07-1-0079 awarded by the United States Air Force Office of Scientific Research. The government has certain rights in the invention.

BACKGROUND

The present specification makes reference to amino acid sequences, which are included in a Revised Sequence Listing (submitted electronically as a .txt file named "Sequence_Listing.txt"). The revised .txt file was generated on Aug. 6, 2013 and is 9 kb in size. The entire contents of the Revised Sequence Listing are herein incorporated by reference.

Devices that comprise a heating element provide a wide range of biomedical and clinical applications, such as thermal therapy. In particular, light-activated heating elements are of great interest for a number of applications, including photothermal therapy, in which electromagnetic radiation is employed to treat various medical conditions.

In addition, implantable medical devices (IMDs) that monitor and treat physiological conditions within the human body have attracted tremendous interest from biologists, physicians and engineers around the globe. IMDs are used in managing a broad range of ailments, and reflect considerable investment in technology and development, including such varied devices as pacemakers and drug delivery systems. The need for miniature, low power, wireless IMDs has surged, and progress has been made in developing micro- and nano-technologies. Despite such progress, improvements are still needed for the long-term stability and functionality of IMDs, including for active devices that need power for their appropriate operation; such as advancing the biocompatibility of the construction and encapsulation materials, and power source solutions for those devices.

SUMMARY OF THE INVENTION

Among other things, the present invention encompasses the recognition that silk-based materials (e.g., silk fibroin) provide a useful component for an improved light-activated heating element when combined with plasmonic nanoparticles. Such combination can produce photothermal device of superior features, as compared to those previously described in the art. Unique properties of silk-based materials allow a broader range of utilities for plasmonic nanoparticles, which provide increased tonability (e.g., control) and precision. Unlike conventional devices that incorporate plasmonic nanoparticles, silk-based devices provide biocompatibility, biodegradability and conformability. Thus, the invention described herein is useful for various applications, including therapeutic applications in which hyperthermia of a tissue (cells, organs, wounds, etc.) is beneficial.

Accordingly, aspects of the present invention provide photothermal elements that comprise a plurality of plasmonic nanoparticles that generate heat when exposed to electromagnetic radiation, and a silk fibroin matrix, within which the plurality of plasmonic nanoparticles is distributed.

In some embodiments, plasmonic nanoparticles are metal particles, such as gold, silver and iron oxide. In some embodiments, plasmonic nanoparticles useful for the invention are substantially spherical in shape. In some embodiments, plasmonic nanoparticles of useful for the invention are substantially rod-shaped.

In some embodiments, average diameter of plasmonic nanoparticles useful for the invention is in a range of about 2 nm and 500 nm.

In some embodiments, plasmonic nanoparticles useful for the invention constitute a mixture of nanoparticles of two or more types, e.g., shapes, sizes, materials, etc.

In some embodiments, plasmonic nanoparticles are solid particles. In some embodiments, plasmonic nanoparticles are shell-shaped. In some embodiments, plasmonic nanoparticles comprise a hollow shell. In some embodiments, plasmonic nanoparticles comprise a core and a shell.

Another aspect of the invention is drawn to a photothermo-electric device. The device comprises a plasmonic nanoparticle-containing surface and a plasmonic nanoparticle-free surface, across which temperature differential can be created upon illuminating the plasmonic nanoparticle-containing surface. In some embodiments, the photothermoelectric device can be adapted to conform to an in vivo surface, such as skin or tissue, surface of a body cavity, and a tumor.

In some embodiments, photothermal elements can be used to generate heat in vivo, e.g., for photothermal therapy. In some embodiments, the photothermal elements are used for tissue bonding. In some embodiments, the photothermal elements are used for thermal therapy. In some embodiments, thermal therapy is for treating pain. In some embodiments, thermal therapy is for treating cancer.

A further aspect of the invention is drawn to converting the generated heat to other form of energy, e.g., electricity for wireless powering of devices. In some embodiments, the devices are implanted micro-devices.

Accordingly, these plasmonic nanoparticle-doped silk fibroin-based materials can be used as an implantable and biodegradable heating element activated by light in various applications ranging from wireless powering to biomedical applications, e.g., wound healing, pain relief, and cell/bacteria killing.

DETAILED DESCRIPTION OF CERTAIN EMBODIMENTS

Figure 1:
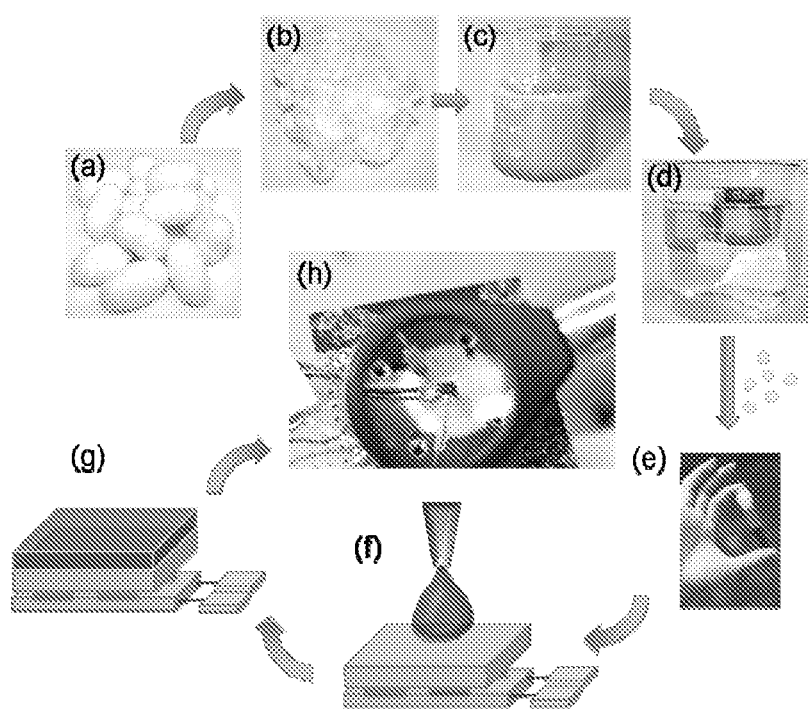
FIG. 1 shows an example of processing and development of a GNP-doped silk film in a non-limiting embodiment of the invention. (1a) Bombyx mori cocoons are cut and boiled in $Na_2CO_3$ to remove sericin (1b) The resulting silk fibroin protein is dissolved in LiBr (1c) before being dialyzed (1d) with water to create and ion-free aqueous silk solution of ~8%. GNPs are made and added to the silk solution before being gently agitated (1e) to create even particle dispersion. Finally, the GNP doped silk solution is cast onto a miniature thermal-electric chip (1f), and allowed to dry (1g and 1h).

For centuries, heat has been recognized for its therapeutic effects for a number of clinical conditions. Development of a small scale heat element which allows controlled heat generation that is also safe for in vivo use is of great interest. Recently, the use of lasers has emerged as promising means of generating heat in a clinical context. For example, light absorbing dyes and particles have been employed for achieving selective heating of local environment, including use in vivo, such as cell and tissues.

The present disclosure provides improved photothermal elements, which comprise plasmonic nanoparticles, such as GNP or gold nanoshells (GNS). Plasmonic nanoparticles resonantly absorb incident light at certain wavelengths and convert it to heat. While the incorporation of plasmonic particles has been used in photothermal therapy techniques for in vivo medical applications such as tumor killing (Hirsch et al., 100 PNAS 13549 (2003)) and pain relief (Jaeger et al., Acta Vet. Scanda. 1 (2007)), selective localization of such nanoparticles for in vivo applications (such as implantation) has posed a technical challenge.

The present invention at least in part provides a solution to the obstacle. According to the invention, photothermal elements comprise plasmonic nanoparticles, which are distributed within a silk fibroin-based matrix, i.e., plasmonic nanoparticle-doped silk materials. The incorporation of silk in a heating element allows the plasmonic nanoparticles to be selectively applied to a site of interest (e.g., a target tissue), where they can be retained for a duration of time in a controlled manner due in part to silk's unique properties, which are briefly discussed below.

Silk fibroin materials offer unique combination of physiochemical properties, e.g., conformability, tackiness, biocompatibility, etc., which in combination allows silk-based materials to function as a biological heating element by providing a matrix to support nanoparticles suspended or dispersed therein.

In addition to its outstanding biocompatibility, silk fibroin matrices have excellent mechanical and optical properties, which make these materials well suited for a variety of implantable medical devices (IMDs). Omenetto & Kaplan, 2 Nature Photonics 641 (2008). Silk fibers, such as those produced by silkworms or spiders, can be processed into silk fibroin which can then be processed into various forms including silk solutions (Jin & Kaplan, 424 Nature 1057 (2003)), gels (Jim et al., 5 Biomacromol. 786 (2004)), foams (Nazarov et al., 5 Biomacromol. 718 (2004)), and films (Jin et al., 15 Adv. Functional Mats. 1241 (2005); Amsden et al., 17 Optics Express 21271 (2009)). Various processing options enable its use as a supporting and packaging material for implanted micro medical devices. Additionally, silk films can be patterned (in both 2D and 3D) to realize a number of optical elements such as diffractive gratings (Amsden et al., 22 Adv. Mats. 1746 (2010)), and wave guides (Parker et al., 21 Adv. Mats. 1 (2009)), within the IMDs.

Furthermore, silk films provide a biologically favorable microenvironment that allow to entrain various biological and/or chemical dopants and maintain their functionality. Proteins (Bini et al., 335 J. Mol. Bio. 27 (2004)), enzymes (Lu et al., 10 Macromol. Biosci. 359 (2010)) and small organics (Lawrence et al., 9 Biomacromol. 1214 (2008)), have been incorporated into silk films for various biochemical functionalities.

Thus, the inclusion of plasmonic nanoparticles in a silk matrix (e.g., silk fibroin matrix) as described herein provides additional utility and opportunities for silk fibroin-based bio-electronics and photonics devices through temperature/heat control. Importantly, silk fibroin can be loaded with higher concentrations of plasmonic nanoparticles than other currently existing polymers, thus allowing more heat generation. Additionally, silk fibroin is a superior dispersion medium, avoiding nanoparticle aggregation that is often problematic in other systems.

Advantageously, the silk fibroin-based photothermal element can be entirely or partially biodegradable and biocompatible. The term "biocompatible" refers in general to materials that are not harmful to the environment or to the subject: the environment can be an in vivo environment or an environment outside the body, for example, in a crop field.

As used herein, the term "biodegradable" refers in general to materials that have a chemical structure that can be altered by common environmental chemistries (e.g., enzymes, pH, and naturally-occurring compounds), including the physiological environment within a human, to yield elements or simple chemical structures, without harm thereto. Biodegradable materials can also be bioerodible. By the term "bioerodible" meant that the material is biodegradable, digestible, or erodible or otherwise dissolvable or degradable in the environment to a form where the material is diminished in size, for example, by chemical, biological (e.g., enzymatic), physical dissolution, or solubilization, to allow elimination of the material from the environment without substantial harm. In some embodiments, the term "biodegradable" as used herein, also encompasses the term "bioresorbable", which generally describes a material that decomposes under physiological conditions to break-down products that can undergo bioresorption into the host subject, e.g., becoming metabolites of the biochemical systems of the host subject. Thus, in some embodiments, the silk fibroin-based IMDs of the present invention need not be retrieved, because they are capable of degrading or eroding into materials or components that are not harmful to the subject. Additionally, silk fibroin can be prepared in an all-aqueous process, further expanding its compatibility with biologics and the environment.

As used herein, the term "silk fibroin" includes silkworm fibroin and insect or spider silk protein. See e.g., Lucas et al., 13 Adv. Protein Chem. 107 (1958). For example, silk fibroin useful for the present invention may be that produced by a number of species, including, without limitation: *Antheraea mylitta*; *Antheraea pernyi*; *Antheraea yamamai*; *Galleria mellonella*; *Bombyx mori*; *Bombyx mandarina*; *Galleria mellonella*; *Nephila clavipes*; *Nephila senegalensis*; *Gasteracantha mammosa*; *Argiope aurantia*; *Araneus diadematus*; *Latrodectus geometricus*; *Araneus bicentenarius*; *Tetragnatha versicolor*; *Araneus ventricosus*; *Dolomedes tenebrosus*; *Euagrus chisoseus*; *Plectreurys tristis*; *Argiope trifasciata*; and *Nephila madagascariensis*.

In general, silk for use in accordance with the present invention may be produced by any such organism, or may be prepared through an artificial process, for example, involving genetic engineering of cells or organisms to produce a silk protein and/or chemical synthesis. In some embodiments of the present invention, silk is produced by the silkworm, *Bombyx mori*.

As is known in the art, silks are modular in design, with large internal repeats flanked by shorter (~100 amino acid) terminal domains (N and C termini) Silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules.

Table 1, below, provides an exemplary list of silk-producing species and silk proteins:

Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as textile.

Silkworm cocoon silk contains two structural proteins, the fibroin heavy chain (~350 k Da) and the fibroin light chain (~25 k Da), which are associated with a family of non-structural proteins termed sericin, which glue the fibroin brings together in forming the cocoon. The heavy and light chains of fibroin are linked by a disulfide bond at the C-terminus of the two subunits (Takei, F., Kikuchi, Y., Kikuchi, A., Mizuno, S. and Shimura, K. (1987) J. Cell Biol., 105, 175-180; Tanaka, K., Mori, K. and Mizuno, S. (1993) J. Biochem. (Tokyo), 114, 1-4; Tanaka, K., Kajiyama, N., Ishikura, K., Waga, S., Kikuchi, A., Ohtomo, K.,

TABLE 1

An exemplary list of silk-producing species and silk proteins
(adopted from Bini et al. (2003), J. Mol. Biol. 335(1): 27-40).

| Accession | Species | Producing gland | Protein |
|---|---|---|---|
| A. Silkworms | | | |
| AAN28165 | Antheraea mylitta | Salivary | Fibroin |
| AAC32606 | Antheraea pernyi | Salivary | Fibroin |
| AAK83145 | Antheraea yamamai | Salivary | Fibroin |
| AAG10393 | Galleria mellonella | Salivary | Heavy-chain fibroin (N-terminal) |
| AAG10394 | Galleria mellonella | Salivary | Heavy-chain fibroin (C-terminal) |
| P05790 | Bombyx mori | Salivary | Fibroin heavy chain precursor, Fib-H, H-fibroin |
| CAA27612 | Bombyx mandarina | Salivary | Fibroin |
| Q26427 | Galleria mellonella | Salivary | Fibroin light chain precursor, Fib-L, L-fibroin, PG-1 |
| P21828 | Bombyx mori | Salivary | Fibroin light chain precursor, Fib-L, L-fibroin |
| B. Spiders | | | |
| P19837 | Nephila clavipes | Major ampullate | Spidroin 1, dragline silk fibroin 1 |
| P46804 | Nephila clavipes | Major ampullate | Spidroin 2, dragline silk fibroin 2 |
| AAK30609 | Nephila senegalensis | Major ampullate | Spidroin 2 |
| AAK30601 | Gasteracantha mammosa | Major ampullate | Spidroin 2 |
| AAK30592 | Argiope aurantia | Major ampullate | Spidroin 2 |
| AAC47011 | Araneus diadematus | Major ampullate | Fibroin-4, ADF-4 |
| AAK30604 | Latrodectus geometricus | Major ampullate | Spidroin 2 |
| AAC04503 | Araneus bicentenarius | Major ampullate | Spidroin 2 |
| AAK30615 | Tetragnatha versicolor | Major ampullate | Spidroin 1 |
| AAN85280 | Araneus ventricosus | Major ampullate | Dragline silk protein-1 |
| AAN85281 | Araneus ventricosus | Major ampullate | Dragline silk protein-2 |
| AAC14589 | Nephila clavipes | Minor ampullate | MiSp1 silk protein |
| AAK30598 | Dolomedes tenebrosus | Ampullate | Fibroin 1 |
| AAK30599 | Dolomedes tenebrosus | Ampullate | Fibroin 2 |
| AAK30600 | Euagrus chisoseus | Combined | Fibroin 1 |
| AAK30610 | Plectreurys tristis | Larger ampule-shaped | Fibroin 1 |
| AAK30611 | Plectreurys tristis | Larger ampule-shaped | Fibroin 2 |
| AAK30612 | Plectreurys tristis | Larger ampule-shaped | Fibroin 3 |
| AAK30613 | Plectreurys tristis | Larger ampule-shaped | Fibroin 4 |
| AAK30593 | Argiope trifasciata | Flagelliform | Silk protein |
| AAF36091 | Nephila madagascariensis | Flagelliform | Fibroin, silk protein (N-terminal) |
| AAF36092 | Nephila madagascariensis | Flagelliform | Silk protein (C-terminal) |
| AAC38846 | Nephila clavipes | Flagelliform | Fibroin, silk protein (N-terminal) |
| AAC38847 | Nephila clavipes | Flagelliform | Silk protein (C-terminal) |

Takagi, T. and Mizuno, S. (1999) Biochim. Biophys. Acta, 1432, 92-103; Y Kikuchi, K Mori, S Suzuki, K Yamaguchi and S Mizuno, Structure of the *Bombyx mori* fibroin light-chain-encoding gene: upstream sequence elements common to the light and heavy chain, Gene 110 (1992), pp. 151-158). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., Adv. Protein Chem., 13: 107-242 (1958)). In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from *Nephila clavipes*. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present invention contain fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds.

Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" hydrophobic blocks are typically separated by segments of amino acids with bulky side-groups (e.g., hydrophilic spacers).

In some embodiments, core repeat sequences of the hydrophobic blocks of fibroin are represented by the following amino acid sequences and/or formulae: (GAGAGS)$_{5-15}$ (SEQ ID NO: 1); (GX)$_{5-15}$ (X=V, I, A) (SEQ ID NO: 2); GAAS (SEQ ID NO: 3); (S$_{1-2}$A$_{11-13}$) (SEQ ID NO: 4); GX$_{1-4}$ GGX (SEQ ID NO: 5); GGGX (X=A, S, Y, R, D V, W, R, D) (SEQ ID NO: 6); (S$_{1-2}$A$_{1-4}$)$_{1-2}$ (SEQ ID NO: 7); GLGGLG (SEQ ID NO: 8); GXGGXG (X=L, I, V, P) (SEQ ID NO: 9); GPX (X=L, Y, I); (GP(GGX)$_{1-4}$ Y)n (X=Y, V, S, A) (SEQ ID NO: 10); GRGGAn (SEQ ID NO: 11); GGXn (X=A, T, V, S); GAG(A)$_{6-7}$GGA (SEQ ID NO: 12); and GGX GX GXX (X=Q, Y, L, A, S, R) (SEQ ID NO: 13).

In some embodiments, a fibroin peptide contains multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide contains between 4-17 hydrophobic blocks.

In some embodiments of the invention, a fibroin peptide comprises at least one hydrophilic spacer sequence ("hydrophilic block") that is about 4-50 amino acids in length. Non-limiting examples of the hydrophilic spacer sequences include:

```
                                        (SEQ ID NO: 14)
          TGSSGFGPYVNGGYSG;

(SEQ ID NO: 15)
          YEYAWSSE;

(SEQ ID NO: 16)
          SDFGTGS;

(SEQ ID NO: 17)
          RRAGYDR;

(SEQ ID NO: 18)
          EVIVIDDR;

(SEQ ID NO: 19)
          TTIIEDLDITIDGADGPI
          and (SEQ ID NO: 20)
          TISEELTI.
```

In certain embodiments, a fibroin peptide contains a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences.

In some embodiments, a fibroin peptide suitable for the present invention contains no spacer.

As noted, silks are fibrous proteins and are characterized by modular units linked together to form high molecular weight, highly repetitive proteins. These modular units or domains, each with specific amino acid sequences and chemistries, are thought to provide specific functions. For example, sequence motifs such as poly-alanine (polyA) and poly-alanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of key components in various silk structures whose positioning and arrangement are intimately tied with the end material properties of silk-based materials (reviewed in Omenetto and Kaplan (2010) Science 329: 528-531).

It has been observed that the beta-sheets of fibroin proteins stack to form crystals, whereas the other segments form amorphous domains. It is the interplay between the hard crystalline segments, and the strained elastic semi amorphous regions, that gives silk its extraordinary properties. Non-limiting examples of repeat sequences and spacer sequences from various silk-producing species are provided in Table 2 below.

TABLE 2

Hydrophobic and hydrophilic components of fibroin sequences (adopted from Bini et al. (2003), J. Mol. Biol. 335(1): 27-40).

| | Hydrophilic blocks | | | Hydrophobic blocks | | |
|---|---|---|---|---|---|---|
| | N-term aa | C-term aa | Hydrophilic spacer (aa) & representative sequence | Range, aa | # of Blocks | Core repeat sequences |
| A. Lepidoptera (Heavy chain fibroin) | | | | | | |
| Bombyx mori | 151 | 50 | 32-33, TGSSGFGPYVNGGYSG, (SEQ ID NO: 14) | 159-607 | 12 | (GAGAGS)$_{5-15}$, (SEQ ID NO: 1); (GX)$_{5-15}$ (X = V, I, A), (SEQ ID NO: 2); GAAS (SEQ ID NO: 3) |
| Bombyx mandarina | 151 | | YEYAWSSE, (SEQ ID NO: 15) | | | |
| Antheraea mylitta | 86 | | SDFGTGS, (SEQ ID NO: 16) | | | |
| Antheraea pernyi | 87 | 32 | | | | |
| Antheraea yamamai | 87 | 32 | 7 RRAGYDR, (SEQ ID NO: 17) | 140-340 | 16 | (S$_{1-2}$A-$_{11-13}$), (SEQ ID NO: 4); GX$_{1-4}$ GGX, (SEQ ID NO:5); GGGX (X = A, S, Y, R, D V, W, R, D), (SEQ ID NO: 6) |
| Galleria mellonella | 189 | 60 | 6-8, EVIVIDDR, (SEQ ID NO: 18) | 75-99 | 13 | (S$_{1-2}$A$_{1-4}$)$_{1-2}$, (SEQ ID NO: 7); GLGGLG, (SEQ ID NO: 8); GXGGXG (X  L, I, V, P), (SEQ ID NO: 9); GPX (X = L, Y, I) |
| B. Arachnida | | | | | | |
| Nephila clavipes | 115 | 89 | | | | |
| Nephila madascariensis | 115 | 89 | 26, TTIIEDLDITIDG ADGPI, (SEQ ID NO: 19) | 260-380 | 5 | (GP(GGX)1-4 Y)n (X = Y, V, S, A), (SEQ ID NO: 10) |
| Argiope trifasciata | | 113 | | | | GRGGAn, (SEQ ID NO: 11) GGXn (X = A, T, V, S) |
| Major ampullata | | | TISEELTI, (SEQ ID NO: 20) | | | |
| Nephila clavipes | | 97 | No spacer | 19-46 | | GAG(A)$_{6-7}$GGA, (SEQ ID NO: 12); GGX GX GXX(X = Q, Y, L, A, S, R), (SEQ ID NO: 13) |
| Gasteracantha mammosa | | 89 | No spacer | | | |
| Argiope aurantia | | 82 | No spacer | | | |
| Nephila senegalensis | | 82 | No spacer | | | |
| Latrodectus geometricus | | 88 | No spacer | | | |
| Araneus diadematus | | 94 | No spacer | | | |

The particular silk materials explicitly exemplified herein were typically prepared from material spun by silkworm, B. Mori. Typically, cocoons are boiled for ~30 min in an aqueous solution of 0.02M Na$_2$CO$_3$, then rinsed thoroughly with water to extract the glue-like sericin proteins. The extracted silk is then dissolved in LiBr (such as 9.3 M) solution at room temperature, yielding a 20% (wt.) solution. The resulting silk fibroin solution can then be further processed for a variety of applications as described elsewhere herein. Those of ordinary skill in the art understand other sources available and may well be appropriate, such as those exemplified in the Table above.

The complete sequence of the Bombyx mori fibroin gene has been determined (C.-Z Zhou, F Confalonieri, N Medina, Y Zivanovic, C Esnault and T Yang et al., Fine organization of Bombyx mori fibroin heavy chain gene, Nucl. Acids Res. 28 (2000), pp. 2413-2419). The fibroin coding sequence presents a spectacular organization, with a highly repetitive and G-rich (~45%) core flanked by non-repetitive 5' and 3' ends. This repetitive core is composed of alternate arrays of 12 repetitive and 11 amorphous domains. The sequences of the amorphous domains are evolutionarily conserved and the repetitive domains differ from each other in length by a variety of tandem repeats of subdomains of ~208 bp.

The silkworm fibroin protein consists of layers of anti-parallel beta sheets whose primary structure mainly consists of the recurrent amino acid sequence (Gly-Ser-Gly-Ala-Gly-Ala)n (SEQ ID NO: 21). The beta-sheet configuration of fibroin is largely responsible for the tensile strength of the material due to hydrogen bonds formed in these regions. In addition to being stronger than Kevlar, fibroin is known to be highly elastic. Historically, these attributes have made it a material with applications in several areas, including textile manufacture.

Fibroin is known to arrange itself in three structures at the macromolecular level, termed silk I, silk II, and silk III, the first two being the primary structures observed in nature. The silk II structure generally refers to the beta-sheet conformation of fibroin. Silk I, which is the other main crystal structure of silk fibroin, is a hydrated structure and is considered to be a necessary intermediate for the preorganization or prealignment of silk fibroin molecules. In the nature, silk I structure is transformed into silk II structure after spinning process. For example, silk I is the natural form of fibroin, as emitted from the *Bombyx mori* silk glands. Silk II refers to the arrangement of fibroin molecules in spun silk, which has greater strength and is often used commercially in various applications. As noted above, the amino-acid sequence of the β-sheet forming crystalline region of fibroin is dominated by the hydrophobic sequence. Silk fibre formation involves shear and elongational stress acting on the fibroin solution (up to 30% wt/vol.) in the gland, causing fibroin in solution to crystallize. The process involves a lyotropic liquid crystal phase, which is transformed from a gel to a sol state during spinning—that is, a liquid crystal spinning process. Elongational flow orients the fibroin chains, and the liquid is converted into filaments.

Silk III is a newly discovered structure of fibroin (Valluzzi, Regina; Gido, Samuel P.; Muller, Wayne; Kaplan, David L. (1999). "Orientation of silk III at the air-water interface". International Journal of Biological Macromolecules 24: 237-242). Silk III is formed principally in solutions of fibroin at an interface (i.e. air-water interface, water-oil interface, etc.).

Silk can assemble, and in fact can self-assemble, into crystalline structures. Silk fibroin can be fabricated into desired shapes and conformations, such as silk hydrogels (WO2005/012606; PCT/US08/65076), ultrathin films (WO2007/016524), thick films, conformal coatings (WO2005/000483; WO2005/123114), foams (WO 2005/012606), electrospun mats (WO 2004/000915), microspheres (PCT/US2007/020789), 3D porous matrices (WO2004/062697), solid blocks (WO2003/056297), microfluidic devices (PCT/US07/83646; PCT/US07/83634), electro-optical devices (PCT/US07/83639), and fibers with diameters ranging from the nanoscale (WO2004/000915) to several centimeters (U.S. Pat. No. 6,902,932). The above mentioned applications and patents are incorporated herein by reference in their entirety. For example, silk fibroin can be processed into thin, mechanically robust films with excellent surface quality and optical transparency, which provides an ideal substrate acting as a mechanical support for high-technology materials, such as thin metal layers and contacts, semiconductor films, dielectric powders, nanoparticles, and the like.

These unique physiochemical properties of silk allows its use in a variety of applications such as those described herein. Furthermore, useful silk materials can be prepared through processes that can be carried out at room temperature and are water-based. Therefore, bio-molecules of interest can be readily incorporated into silk materials.

In addition, silk-based materials can be prepared to be smooth and/or adhesive at the molecular level. In some embodiments, silk-based materials provided by and/or utilized in accordance with the present invention are both smooth and adhesive at the molecular level. Silk-based materials showing molecular level smoothness and/or adhesiveness permit certain applications that are not possible with other materials. Surface smoothness/roughness plays an important role in determining how a real object will interact with its environment. In certain embodiments, silk-based materials provided by and/or used in accordance with the present invention have affinity for biological surfaces, e.g., cells and soft tissues. Moreover, silk-based materials provided by and/or utilized in accordance with certain embodiments of the present invention exhibit excellent adhesion to conductive materials, such as metal. The present invention embraces the recognition that certain silk materials can act as in interface between a biological element and a non-biological element (e.g., metal-based particles).

In accordance with certain embodiments of the invention, some provided silk-based materials can be prepared to show tackiness (e.g., stickability) when wet. This property, particularly when coupled with surface smoothness as described herein, can render certain silk materials uniquely suitable to serve as nano- and/or micro-scale adhesives that attach (e.g., glue) a non-biological element (e.g., nanoparticles) with a biological surface in a way other matrices cannot.

While a number of types of silk fibroin, such as those exemplified above, may be used to practice the claimed invention, silk fibroin produced by silkworms, such as *Bombyx mori*, is the most common and represents an earth-friendly, renewable resource. For instance, silk fibroin may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that may be used.

As already noted, an aqueous silk fibroin solution may be prepared using techniques known in the art. Suitable processes for preparing silk fibroin solution are disclosed, for example, in U.S. patent application Ser. No. 11/247,358; WO/2005/012606; and WO/2008/127401. The silk aqueous solution can then be processed into silk matrix such as silk films, conformal coatings or layers, or 3-dimensional scaffolds, or electrospun fibers. A micro-filtration step may be used herein. For example, the prepared silk fibroin solution may be processed further by centrifugation and syringe based micro-filtration before further processing into silk matrix.

As a basis for generating heat useful for the present invention, certain nano-scale heating elements, such as plasmonic nanoparticles (e.g., GNP and gold nanoshells (GNS)), may be used. The art is familiar with plasmonic nanoparticles. Briefly, plasmonic nanoparticles resonantly absorb incident light at certain wavelengths and convert it to heat. To date, plasmonic particles have been used in photothermal therapy techniques for in vivo medical applications, such as tumor killing (Hirsch et al., 100 PNAS 13549 (2003)) and pain relief (Jaeger et al., Acta Vet. Scanda. 1 (2007)).

Thus, aspects of the present invention provide for a photothermal element comprising plasmonic nanoparticles incorporated into or distributed within a silk fibroin matrix, such that the plasmonic nanoparticles absorb at least a portion of incident radiation to generate heat when the element is exposed to the electromagnetic radiation. In some embodiments, photothermal elements described herein may be adapted to conform to a surface upon contact with the surface. In some embodiments, such surfaces include biological surfaces, such as cells and tissues.

The silk fibroin matrix can be optically transparent. Additionally, depending on various applications, the silk fibroin matrix can be shaped into different forms, e.g., a wire, a fiber, a film, an ultrathin film, a gel, an injectable matrix, a coating, a vesicle, a sponge, a block, or a porous structure. In some embodiments, the silk fibroin matrix can be used to produce an optical fiber. In some embodiments, a silk fibroin matrix can be made piezoelectric. In some embodiments, the silk fibroin matrix is a film having a thickness of 10 nm or less, such as about 10 nm, about 9 nm, about 8 nm, about 7 nm, about 6 nm, about 5 nm, etc. In some embodiments, the silk fibroin matrix is a film having a thickness of 30 nm to 500 µm; 30 nm to 50 nm; about 100 nm; about 2 µm; or about 20 µm to about 30 µm. In one embodiment, the silk fibroin film has a thickness of about 30 µm.

Metal-based nanophotonics (plasmonics) is a field concerned with manipulating and focusing light on nanoscale structures that are much smaller than conventional optical components. These optically heatable nanoparticles are capable of converting at least a portion of incident radiation into heat energy when such nanoparticles are exposed to the electromagnetic radiation. Plasmonic technology has the potential to be used in applications such as nanoscale optical interconnects for high performance computer chips, highly efficient thin-film solar cells, and extremely sensitive biomolecular sensors. As described in further detail herein, the plasmonic nanoparticles of the present embodiments can be engineered to achieve peak resonance at a given wavelength of light.

According to the invention, the "plasmonic nanoparticles" useful for the present invention are plasmon resonant nanoparticles, typically metallic particles or metal-incorporated particles, that respond to electromagnetic radiation. Without wishing to be bound by a particular theory, the plasmonic nanoparticles respond to electromagnetic radiation because the conduction electrons in the metal undergo a collective resonance called a surface plasmon resonance. The magnitude, peak wavelength and spectral bandwidth of the plasmon resonance associated with a particular plasmonic nanoparticle may be dependent on the nanoparticle's size, shape, and/or material composition, as well as its local dielectric environment. See, e.g., Lu et al., *Chemical Synthesis of Novel Plasmonic Nanoparticles*, 60 Ann. Rev. Phys. Chem. 167 (2009). These factors allow for predetermined control of a plasmonic nanoparticle's thermal activity in response to a specific wavelength of electromagnetic radiation.

The plasmonic nanoparticles of the present invention can be of any shape (e.g., configuration), for example, nanoshells, semishells or nanobowls (Ye et al., 113 J. Phys. Chem. C 3110 (2009); Ye et al., 25 Langmuir 1822 (2009); Ye et al., ACS 4 Nano 1457 (2010)); nanorods (Baciu et al., *Protein-Membrane Interaction Probed by Single Plasmonic Nanoparticles*, 8 Nano Lett. 1724 (2008)); hollow nanocages, open nanocages or hollow nanospheres (Ye et al., 15 Optics Express 23765 (2009); Cobley et al., *Targeting gold nanocages to cancer cells for photothermal destruction and drug delivery*, 7 Expert Opin. Drug Deliv. 577 (2010)); nanocrystals; nanopowders; or nanocages. The plasmonic nanoparticles can be produced as taught herein or by techniques known in the art; or can be purchased from a wide selection of commercial sources including nanoComposix, Inc. (San Diego, Calif.) NN-Labs, LLC (Fayetteville, Ark.), Nanoshel LLC (Haryana, Indian; TedPella, Inc. Redding, Calif.), and Nanomaterial Store (Fremont, Calif.).

Accordingly, in some embodiments, the nanoparticles of the present invention can be nanoshells. Metal nanoshells possess optical properties similar to metal colloids, e.g., a strong optical absorption and an extremely large and fast third-order nonlinear optical (NLO) polarizability associated with their plasmon resonance. In one example, a nanoshell can be composed of a dielectric core (silica), coated with an ultrathin metallic layer (e.g., gold); another example of a nanoshell can comprise a gold sulfide core and a gold shell. See, e.g., U.S. Pat. No. 6,428,811. Examples of dielectric core materials include, but are not limited to, silicon dioxide, gold sulfide, titanium dioxide, polymethyl methacrylate (PMMA), polystyrene, and macromolecules such as dendrimers. The core material can also be a silk fibroin nanoparticle, see PCT/US2010/05069, Silk Nanospheres & Microspheres & Methods of Making Same, filed Sep. 29, 2010. By adjusting the relative core and shell thickness and/or core and shell material, nanoshells can absorb or scatter light at a desired wavelength or across a particular wavelength spectrum (e.g., visible and near infrared wavelengths).

The plasmonic nanoparticle typically comprises at least one metal. In some embodiments, a useful plasmonic nanoparticle is typically a metal or an alloy, or is doped with at least one metal or an alloy. Such metal can be any art-recognized metal in that excitation of surface plasmon can be induced by light. In some embodiments, the metal can be a noble metal, including, but not limited to, gold, silver, ruthenium, rhodium, palladium, osmium, iridium, and platinum. Depending on the application, in some embodiments, the noble metal can possibly be mercury. In some embodiments, useful metal can be a non-noble metal, such as titanium, aluminum, nickel, fluorine, cerium, tin, bismuth, antimony, molybdenum, chromium, cobalt, zinc, tungsten, polonium, rhenium and copper. In some embodiments, the plasmonic nanoparticles can comprise oxides of noble or non-noble metals. In some embodiments, the plasmonic nanoparticles can comprise alloys of noble metals and/or non-noble metals, or non-homogeneous mixtures of such metals. In some embodiments, the plasmonic nanoparticles can comprise silica or silk fibroin doped with rare earth emitters, such as $Pr^{+3}$, $Er^{+3}$, or $Nd^{+3}$. See, e.g., U.S. Pat. No. 6,530,944. In one embodiment, the plasmonic nanoparticles comprise gold. In one embodiment, the plasmonic nanoparticles are gold nanoparticles.

The size of the plasmonic nanoparticles can be adapted to resonantly absorb a specific wavelength of light at a desirable absorbance level when the plasmonic nanoparticles are exposed to electromagnetic radiation. In some embodiments, the plasmonic nanoparticles can have a diameter of about 1 nm to about 1000 nm, about 5 nm to about 500 nm, about 5 nm to about 250 nm, or about 5 nm to about 100 nm, or about 5 nm to about 50 nm. In some embodiments, the plasmonic nanoparticles have a diameter of about 5 nm to about 25 nm. As used herein, the term "diameter" in reference to a population of plasmonic nanoparticles means the average diameter of the population. In some embodiments, the term "diameter" can refer to the maximum size of the plasmonic particle within the population. In other embodiments, the term "diameter" can refer to the minimum size of the plasmonic particle within the population. If the population is homogenous in size, the term "diameter" can also refer to the diameter of each individual particle.

In some embodiments, a population of plasmonic nanoparticles is a heterogeneous population, such that the population contains particles of varying diameters. In some embodiments, such variation in diameters within a population of nanoparticles is within +/−100%, 90%, 80%, 70%, 60%, 50%, 40%, 30%, 20%, 15%, 10%, 5%, 2%, or less.

It is known in the art that, at the nanoscale, bulk (e.g., solid) metals exhibit optical resonances of their surface plasmons. In colloidal form, these metals typically absorb and scatter light strongly at a characteristic wavelength (plasmon resonance) in the visible region of the spectrum. The ability to work with wavelengths in the near infrared (NIR) region of the spectrum may be for certain applications clinically meaningful because light penetrates deep within tissue (up to several centimeters) at these wavelengths. Indeed, certain geometries (spheres, rods and shells) of metal nanoparticles have optical plasmon resonances that can be tuned to the NIR region (Oldenburg et al. 1999). While gold nanospheres and nanorods are made of solid gold, nanoshells consist of a dielectric core (e.g. silica) surrounded by a thin gold shell. Nanospheres exhibit resonances around 540 nm without much tunability of this peak whereas nanoshells and nanorods have peak resonances that can be tuned throughout the NIR spectrum (Jain et al. 2006; Oldenburg et al. 1998). Nanoshells are tuned via their core-to-shell ratio while nanorods are tunable through their aspect ratio (i.e. ratio of the length to diameter). For instance, gold nanoshells comprised of an aminated colloidal silica (120 nm diameter) core with a 14-nm-thick shell of gold colloid adsorbed onto it as sequential nucleating sites result in an absorption peak between 780 and 800 nm.

Figure 2:
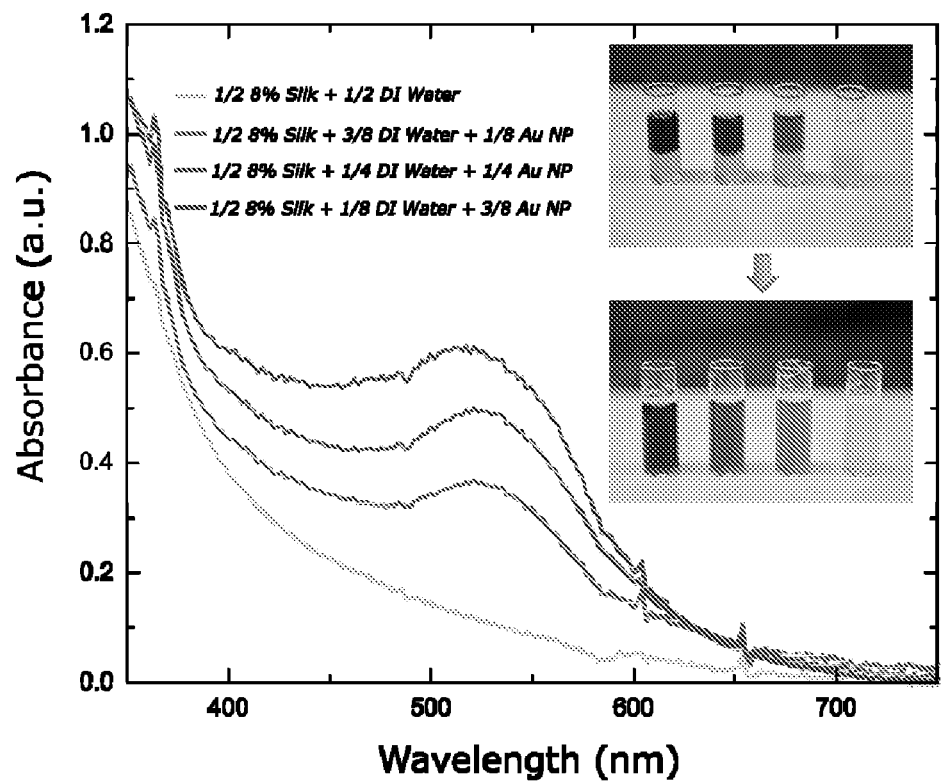
FIG. 2 is a graph depicting characteristic ultraviolet-visible (UV-Vis) spectra between 350 nm and 750 nm for different concentrations of GNP-doped silk matrices. With increasing concentration of GNPs, the light absorption of the sample at ~530 nm increases dramatically. Colorimetric differences between the samples are also visible to the naked eye.

The art is familiar with suitable methods by which optimal wavelengths or a range thereof may be determined FIG. 2 provides an exemplary graph showing the relationship between absorbance and relative concentrations of gold nanoparticles dispersed in a silk fibroin solution in the UV-visible spectra. As shown in FIG. 2, when an 8% silk fibroin solution is prepared and is mixed with gold nanoparticles as described in Example 1 below, the absorption of the sample at about 530 nm increases dramatically. By varying at least one variable, such as nanoparticle concentrations, gradient, particle size, shape, one of ordinary skill in the art can adjust an effective range of wavelengths and absorbance suitable for particular applications.

Figure 3:
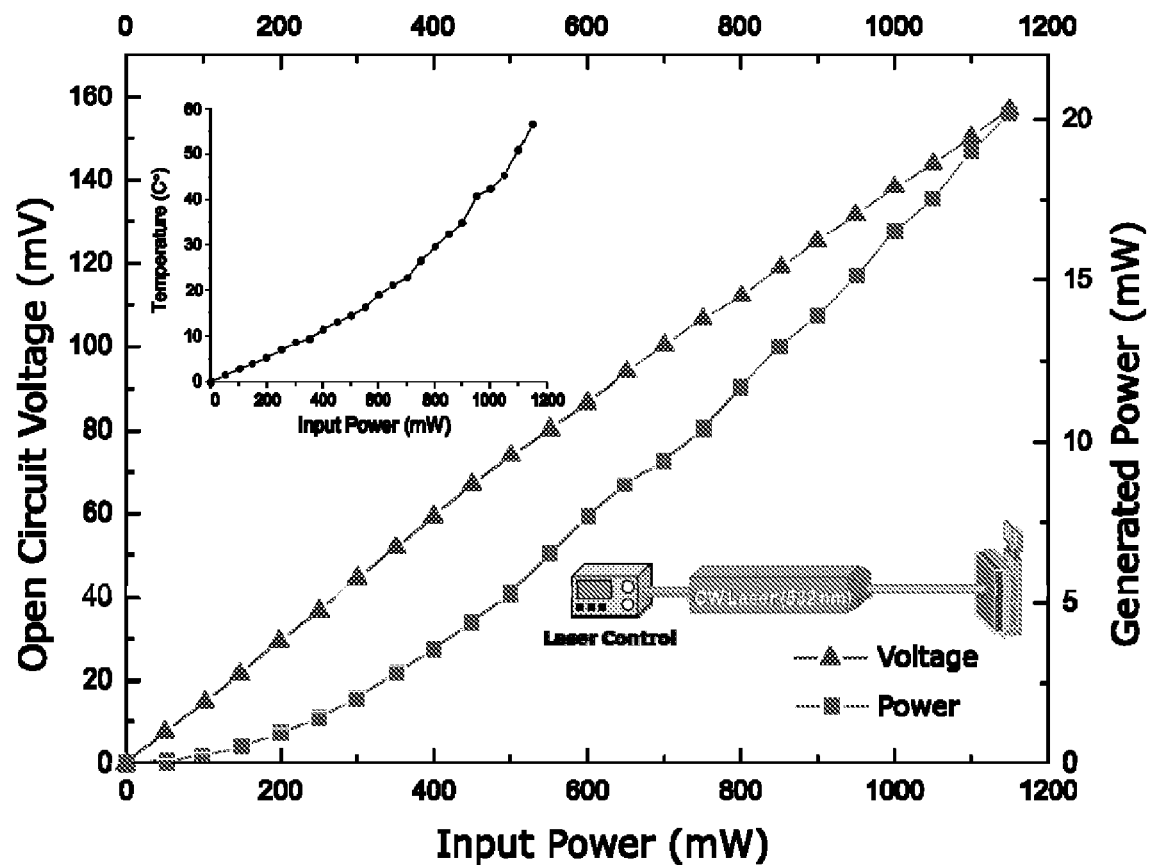
FIG. 3 presents data reflecting open circuit voltage (triangle) and generated power (square) of the thermal-electric element as a function of laser input power for one particular embodiment of the invention (bottom inset). Temperature increase vs. Input power is also shown in the upper inset.

It should be appreciated that for generating useful amounts of heat suitable for particular applications, factors such as nanoparticle concentrations in a silk matrix and/or input power may be altered. In a non-limiting example, the relationship between varying degree of input power and corresponding thermal power is provided in FIG. 3, which is discussed in more detail below. It should be noted that increasing a nanoparticle concentration within a silk matrix should yield a closely proportional and near linear increase in heat generation within an effective range. Thus, for applications that require relatively high heat generation (such as would bonding), it is contemplated that higher concentrations of plasmonic nanoparticles should be incorporated in a silk matrix preparation. Additionally or alternatively, greater power input can be used to achieve the amount of heat generation desired. Generated heat differentials may be measured by, for example, casting a plasmonic nanoparticle-doped silk matrix on a thermal-power chip and monitoring the temperature difference created across a silk-associated surface and non-silk-associated surface upon illumination. This is illustrated in FIG. 3.

As mentioned, the invention described herein is useful for implantable medical devices (IMDs) that monitor and treat physiological conditions within a human body. IMDs broadly have attracted tremendous interest from biologists, physicians, and engineers around the globe. IMDs are utilized to manage a broad range of ailments, including, but not limited to, diabetes (Jaremko & Rorstad, 21 Diabetes Care 444 (1998)), arrhythmia (Hsia et al., 87 Annals Thoracic Surg. 124 (2009)), and Parkinson's disease (Singh et al., 81 Adv. Treat. Parkinson's Dis. 29 (2007)). The need for miniature, low power, wireless IMDs has surged, and progress has been made in the past two decades encompassing micro- and nano-technologies. See Staples et al., 23 Pharm. Res. 847 (2006); Lu & Chen, 56 Adv. Drug Deliv. Rev. 1621 (2004); Hilt & Peppas, 306 Intl. J. Pharm. 15 (2005). Despite these advances, improvements are still needed in the long-term stability and functionality of IMDs, especially for active devices that need power for their appropriate operation. The necessary improvements, addressed herein, involve advancing the biocompatibility of the construction and encapsulation materials for those devices, as well as power source solutions. In some embodiments, these IMDs can incorporate the aspects of the present invention based on the instant specification. Exemplary IMDs include, but are not limited to, pacemakers (Narazaki & Yamashita, 29 Inflammation & Regeneration 123 (2009)); cardiac defibrillators (McAlister et al., 152 Evidence Report/Tech. Assessment 1 (2007)); nerve stimulators (Mobbs et al., 14 J. Clin. Neurosci. 216 (2007)); and drug delivery systems (Elman et al., 11 Biomedical Microdevices 1387 (2009)).

For implantation utility, absorption, as exemplified in the Examples, peaks at wavelengths close to 532 nm by tissue chromophores, such as hemoglobin and melanin, may create limitations on the penetration depth of the laser when coupled with these tissue chromophores. In order to reach an implant deeper than approximately 0.5 mm, the power would need to be increased to unsafe levels, which may cause tissue damage or burns. Hamlin & Demidova, 6140 Proc. SPIE 1 (2006). In addition, water can act as a chromophore at wavelengths longer than 1150 nm, thus leaving an available "optical window" between about 600 nm and about 1150 nm with low levels of absorption. Id. Accordingly, in some embodiments, the plasmonic nanoparticles of the invention can be tuned to be resonant at any wavelength between about 600 nm and about 1150 nm. In some embodiments, the plasmonic nanoparticles can be tuned to be resonant at longer wavelengths, such as about 670 nm, about 830 nm, or about 1064 nm. Stolik et al., 57 J. Photochem. Photobio. B: Bio. 90 (2000). This can be accomplished, for example, by changing the diameter of the plasmonic nanoparticles or using nanoshells for longer penetration depths. Prodan et al., 3 Nano Lett. 1411 (2003). At these wavelengths, the absorption rate of body tissues will be relatively low, so that safe power levels will be possible even for deeply implanted devices.

The plasmonic nanoparticles can be distributed within or on the silk fibroin matrix in great variation to optimize photothermal activity for a particular use. In some embodiments, the plasmonic nanoparticles can be evenly distributed within or on the surface of the silk fibroin matrix. In some embodiments, the plasmonic nanoparticles can be distributed in a gradient within or on the silk fibroin matrix, e.g., more plasmonic nanoparticles can be selectively distributed within or on one portion of the silk fibroin matrix. In some embodiments, the plasmonic nanoparticles can be distributed in a pattern such as an optical pattern, a micropattern, or a nanopattern. See, e.g., Dong et al., *Biogenic synthesis of hierarchical hybrid nanocomposites and patterning of silver nanoparticles,* 110 Mats. Chem. Phys. 160 (2008). The pattern can be achieved by any known technique, such as nanoprinting or etching, and allows for corresponding patterned photothermal or photothermal-electric generation. Such gradients or patterns provide for control of photothermal or thermo-electric energy in a predetermined fashion. In other words, dosages and locations of energy delivery can be designed and integrated into the silk fibroin matrix by selective distributing or patterning of the plasmonic nanoparticles.

In some embodiments, plasmonic nanoparticles can further comprise an additional material. The additional material can be selected based upon the choice of the metal used in the plasmonic nanoparticles, the desirable wavelength of the resonant peak, the absorbance magnitude, the spectrum bandwidth, and/or other desirable properties of the plasmonic particles, e.g., magnetic properties. In some embodiments, the additional material can be silk fibroin. Silk fibroin nanoparticles can be produced as taught, for example, in Zhang et al., *Formation of silk fibroin nanoparticles in water-miscible organic solvent and their characterization,* 9 J. Nanoparticle Res. 885 (2007); Gupta et al., 4 Intl. J. Nanomed. 117 (2009); Kharlampieva et al., *Silk-based Mechanically-robust LbL Nano-composites with Tailored Optical Properties,* 101 PMSE Preprints 1059 (2009).

In some embodiments, photothermal elements described herein can include at least one active agent, e.g., within the silk fibroin matrix and/or in the plasmonic nanoparticles. Examples of the active agent include, without limitations, organic materials such as horseradish peroxidase, phenolsulfonphthalein, oligonucleotides, nucleic acids, aptamers, antibodies or antibody-like molecules (e.g., fragments of antibodies, single-chain antibodies (scFv), single domain antibodies, chimeric antibodies, and diabodies), enzymes (for example, peroxidase, lipase, amylose, organophosphate dehydrogenase, ligases, restriction endonucleases, ribonucleases, RNA or DNA polymerases, glucose oxidase, and lactase), cells (including red blood cells and stem cells), viruses, other proteins, or peptides, peptidomimetics, small molecules (e.g., drugs, dyes, amino acids, vitamins, antioxidants), biosimilars, biologics, lipids, carbohydrates, chromophores, light emitting organic compounds (such as luciferin, carotenes) and light emitting inorganic compounds (e.g., chemical dyes and/or contrast enhancing agents such as indocyanine green), antibiotics, antifungals, antivirals, light-harvesting compounds such as chlorophyll, bacteriorhodopsin, proteorhodopsin, and porphyrins and related electronically active compounds, or pro-drugs, analogs, and any combinations of any of the foregoing. See, e.g., WO 2011/006133, Bioengineered Silk Protein-Based Nucleic Acid Delivery Systems; WO 2010/141133, Silk Fibroin Systems for Antibiotic Delivery; WO 2009/140588, Silk Polymer-Based Adenosine Release: Therapeutic Potential for Epilepsy; WO 2008/118133, Silk Microspheres for Encapsulation & Controlled Release; WO 2005/123114, Silk-Based Drug Delivery System.

In some embodiments where the photothermal element is used for treating tissues, the silk fibroin can include at least one factor that can facilitate treatment of tissues, e.g., wound healing. Such factors include, without limitations, albumin, fibrinogen, collagen, elastin, fibronectin, laminin, chitosan, fibroblast growth factor, vascular endothelial cell growth factor, platelet-derived growth factor, epidermal growth factor, insulin-like growth factor, and any combinations thereof. In some embodiments, the active agents or factors described herein can be further encapsulated into a different silk fibroin carrier, e.g., microparticles, nanoparticles, films or porous sponges, that can regulate the release of the active agent or the factor, before distributed in the silk fibroin matrix of the photothermal element. See e.g., WO 2008/118133; WO 2009/140588; WO 2011/008842, Electrospun Silk Material Systems for Wound Healing. In some embodiments where a specific tissue or organism is targeted, at least a portion of the silk fibroin matrix, the plasmonic nanoparticles, and/or the silk fibroin carriers can be further bound to one or more targeting moieties. Exemplary targeting moieties include, but are not limited to, an antibody, fragments of antibodies, ligands for specific receptors or proteins that can bind specifically to the organism, cell, or tissue. See, e.g., U.S. Pat. No. 6,685,730; U.S. Pat. No. 6,530,944.

Additionally, the silk fibroin matrix can be optionally combined with one or more biocompatible polymers. Non-limiting examples of biocompatible polymers include polyethylene oxide, polyethylene glycol, collagen, fibronectin, keratin, polyaspartic acid, polylysine, alginate, chitosan, chitin, hyaluronic acid, and any combinations thereof. See, e.g., WO 04/062697; WO 05/012606. Any other biocompatible polymers known to a skilled artisan can also be combined with the silk fibroin matrix. Silk fibroin can also be chemically modified with active agents in the solution, for example through diazonium or carbodiimide coupling reactions, avidin-biotin interaction, or gene modification and the like, to alter the physical properties and functionalities of the silk fibroin protein. See, e.g., WO 2011/011347, Functionalization of Silk Material by Avidin-Biotin Interaction; WO 2010/057142, Surface Modification of Silk Fibroin Matrices with PEG Useful as Anti-Adhesion Barriers & Anti-Thrombotic Materials; U.S. Ser No. 12/192,588, Diazonium Salt Modification of Silk Polymer. For example, the surface of the silk fibroin matrix can be modified with active agents such as enzymes or cytokines through carbodiimide-mediated reactions to form gradient of the active agents within the silk fibroin matrix. See, e.g., U.S. Patent Pub. No. 2007/0212730, Covalently immobilized protein gradients in 3-dimensional porous scaffolds. Additionally, the silk fibroin matrix can be combined with at least one agent, such as glycerol, that, e.g., affect flexibility of the matrix. See, e.g., WO 2010/042798, Modified Silk films Containing Glycerol.

Accordingly, the present invention provides for methods for the localized delivery of heat and the localized imaging of biological materials, e.g., cells and/or tissues. The delivery can be in vitro or in vivo, and is useful for the localized treatment of a disease or disorder, e.g., cancer, inflammation, or other disorders involving over-proliferation of tissue. The method involves localized induction of heat to a cell or tissue by delivering to said cell or tissue a conformal silk fibroin matrix comprising plasmonic nanoparticles and exposing the plasmonic nanoparticles to an excitation source under conditions wherein they emit heat. One embodiment of the invention includes a method for inducing localized heat to a cell or tissue. The method includes delivering the photothermal element described herein to cells or tissue; and exposing said photothermal element to electromagnetic radiation, such as ultraviolet, visible, infrared, or any combination thereof, wherein the plasmonic nanoparticles emit heat upon exposure to said electromagnetic radiation. The method can also be useful for diagnostic imaging alone, or in combination with photothermal therapy. See Hirsch et al., 100 PNAS 13549 (2003).

Additionally, in some embodiments of the present invention, the photothermal element provides for a system that can modulate in vivo delivery of an agent. The system includes a plurality of plasmonic nanoparticles, capable of converting incident radiation into heat energy when the nanoparticles are irradiated with electromagnetic radiation, contained in a silk fibroin matrix that can further comprise at least one active agent distributed therein. By way of example, when the temperature of the silk fibroin matrix or portion thereof is at a first temperature (e.g., 37° C.), the active agent is retained within the silk fibroin matrix. When the silk fibroin matrix or a portion thereof is raised to a second, higher temperature (e.g., ~40° C.-45° C.), i.e., heat generated by plasmonic particles exposed to electromagnetic radiation, at least a portion of the active agent can be released from the silk fibroin matrix into the body. Optionally, embodiments of the invention can include a biosensor system, e.g., for providing information about in vivo status to assist in making treatment decisions. An advantage of the system is the ability to locally change the temperature of a thermally-responsive IMD by exposure to light targeted for absorption and conversion to heat by plasmonic nanoparticles (including, e.g., metal nanoshells). This allows implantation of a drug delivery device with multiple dosages, and provides for an external control over the dosage profiles by regulating exposure of the drug delivery device to an appropriate light source.

Another aspect of the invention relates to a method of photothermally modulating in vivo delivery of an active agent. The method includes implanting into the body of a subject in need of treatment, a composition or a device containing one or more plasmonic nanoparticles and at least one active agent in a silk fibroin matrix. The active agent can be substantially retained by the silk fibroin matrix when the temperature of the composition is at about normal body temperature of the subject. At least a portion of the active agent can be substantially released from the silk fibroin matrix into the body of the subject when the temperature of the composition, or a portion thereof, is raised. The method includes applying electromagnetic radiation, such as near-infrared radiation, to the implanted composition or device from outside the body. The electromagnetic radiation can be applied through an optical grid. The amount and duration of electromagnetic radiation can be applied until it is sufficient to raise the temperature of the plasmonic nanoparticles such that the silk fibroin matrix, or a portion thereof, can cause release of the agent to commence. Alternatively, application of the electromagnetic radiation can be continued until a desired amount of the active agent has been released from the implant into the body. After the desired amount of the agent has been delivered, the composition can be allowed to return to normal body temperature, whereupon drug delivery is reduced or ceased, as desired. In some embodiments, the application of electromagnetic radiation can be repeated at a later time, if multiple dosing is desired. In some embodiments, the treatment method can further comprise applying ultrasound, magnetic fields, electric fields, or any combinations thereof, to the implanted composition or device from outside the body. The silk fibroin matrix is biocompatible and biodegradable, and does not require subsequent removal. The implantation can be subcutaneous or parenteral.

Another embodiment of the invention provides for a method of enhancing wound healing, such as tissue welding. For example, laser tissue welding refers to techniques by which tissues can be joined in response to exposure to light and the subsequent generation of heat. The goal of these techniques is the rapid joining of tissues with high tensile strength across the union, a tissue union throughout the depth of the targeted tissue, a minimum of scar tissue formation, and minimal damage to surrounding tissue. These techniques can also be beneficial in a number of minimally invasive surgical techniques. Laser tissue repair has application in many surgical disciplines for procedures such as closure of skin wounds, vascular anastomosis, ocular repair, nerve repair, cartilage repair, and liver repair. Currently, laser tissue repair is accomplished either through welding, apposing two tissue surfaces and then exposing to laser radiation to heat the tissues sufficiently to join them, or through soldering, wherein an exogenous material such as a protein or synthetic polymer is placed between two tissue surfaces to enhance joining of the tissues upon exposure to laser radiation. Temperatures greater than 50° C. can induce tissue union, which can be likely induced by the denaturation of proteins and the subsequent entanglement of adjacent protein chains. See, e.g., U.S. Pat. No. 6,685,730. In accordance with methods of the invention, the conformal photothermal element as described herein can be contacted with the tissue, and irradiated to transfer heat to the target tissue. See also WO 2010/065957, Vascularized Living Skin Constructs & Methods of Use Thereof, WO 2011, Electrospun Silk Material Systems for Wound Healing.

Accordingly, plasmonic nanoparticle-doped silk fibroin matrix may be used to achieve heat-based bonding of a wound. Thus, the invention includes silk-based "stitchless sutures" which can be controlled by illumination of a target wound site so as to generate light-activated heat which aids in bonding or welding of a wound or tissue. For example, useful embodiments of the invention for the contemplated utility include a composition comprising photothermal plasmonic nanoparticles dispersed within a silk-based material, such as a gel and film, so as to form plasmonic nanoparticle-dosed silk matrix. Such a plasmonic nanoparticle-dosed silk matrix can be applied to a site of would or tissue to be repaired, e.g., along the edges of an open wound or tissues to be bonded. The site is then illuminated with a suitable light source to induce heat generation, with little or no adverse effects to surrounding tissues.

As mentioned above, conventionally, the laser technology has been employed for achieving heat-based bonding of tissues, which is sometimes referred to as "laser-bonded healing." While laser can also provide pinpoint precision to localize the beam to a very small area within a target tissue, challenges have been that such technique is prone to cause overheating of a target tissue or wound. By contrast, silk-based "stitchless sutures" realized by the present invention provides a means of precisely controlling not only the location of application but the temperatures to be applied to a target tissue. Typically, it is desirable to apply heat in a range of approximately 55° C. to approximately 70° C. to a would to be bonded, which is thought to be the optimal range of temperatures at which flesh melts but can still heal. In some embodiments, a concentration of plasmonic nanoparticles within a silk matrix is selected such that when the particles absorb light at a given intensity, they generate heat of about 60-68° C., about 63-67° C., e.g., 60° C., 61° C., 62° C., 63° C., 64° C., 65° C., 66° C., 67° C. and 68° C. In some embodiments, a concentration of plasmonic nanoparticles within a silk matrix is selected such that when the particles absorb light at a given intensity, they generate heat of about 65° C.

In some embodiments, tissue repair as described herein is performed to aid wound healing, such as an open cut on the skin. In some embodiments, tissue repair is performed as described herein as part of a surgical procedure. For example, the invention may provide better tools for non-invasive surgical procedures in which conventional stitching of internal tissues poses a challenge.

In principle, use of plasmonic nanoparticles-doped silk matrix for such applications is thought to allow more rapid healing and/or less scarring, as compared to classic needle-and-thread sutures. Moreover, such procedure may also reduce risk of infection and/or inflammation.

In other embodiments, the invention includes use of plasmonic nanoparticles-doped silk matrix for clinical hyperthermia. Laser heating sources ranging from radio frequency or microwaves as well as ultrasound waves were introduced to induce moderate heating in specific target region. This is generally referred to as hyperthermia, which is typically defined as heating of tissue to a temperature usually in the range of 41 to 47° C. for tens of minutes (Svaasand et al., 1990. Lasers Med Sci 5:121-128).

In some embodiments, hyperthermia is achieved according to methods described herein to provide temperatures between about 40° C. and 45° C. It has been reported that mild elevation of temperature in such a range can mediate certain therapeutic effects, including but are not limited to pain relief and anti-tumor effects. In particular, effectiveness of hyperthermia-mediated cancer treatment has been documented. Traditionally, hyperthermia can be achieved in a number ways, including local hyperthermia by external or internal energy sources, regional hyperthermia by irrigation of body cavities or perfusion of organs or limbs, and whole body hyperthermia. For prostate cancer treatment, for example, techniques such as intraluminal or intracavitary treatments have been employed successfully in the treatment of locally advanced prostate cancer using modalities such as ultrasound, radiofrequency and microwaves with appropriate applicators positioned either externally, intraluminally or interstitially to generate heat (Krishman et al., 2010. "Nanoparticle-mediated thermal therapy: Evolving strategies for prostate cancer therapy" Int J Hyperthermia. 26(8): 775-89). By using the invention described herein, targeting tumors such as prostate cancer may be realized more effectively and with higher efficacy.

Another embodiment provides for a method for diagnostic imaging of at least one cell or a tissue comprising delivering a plasmonic nanoparticle-doped silk fibroin matrix to the cell or the tissue, and exposing said plasmonic nanoparticles to electromagnetic radiation under conditions wherein said plasmonic nanoparticles absorb and/or scatter light to be detected by a photodetector. In some embodiments, the plasmonic nanoparticle-doped silk-fibroin matrix can be coated with a targeting moiety, e.g. against tumor-specific antigens presents on the tumor cell surface for detection of cancer cells. The electromagnetic radiation can be light of any wavelength, e.g., ultraviolet, visible, or infrared radiation. The plasmonic nanoparticles can act as contrast agents with respect to said electromagnetic radiation. See also WO 2009/105537, Non-invasive Optical Characterization of Biomaterial Mineralization.

One of ordinary skill in the art will appreciate that the heat generated by the photothermal silk fibroin matrix can be used to change or alter the structure of the silk fibroin matrix, e.g., to convert the silk fibroin to β-sheet structure, or increase the amount of β-sheet structure in the silk fibroin matrix. In this aspect, the silk fibroin matrix can undergo a phase transition in response to exposure to electromagnetic radiation. For example, the photothermal element can be in a gel or a liquid form such that it can be injected or easily implanted into a subject at a chosen site of action where the photothermal element can conform to the shape of the tissue or cavity targeted. Once injected or implanted, the photothermal element can be irradiated with electromagnetic radiation such that the silk fibroin matrix is heated as to adopt β-sheet structure which is more solid and less soluble in nature. Those of ordinary skill in the art will appreciate that various structural features of the element contribute to its degree of surface conformability, and will be readily able to adjust such features in order to achieve a particular desired level of conformability.

Although photothermal tumor ablation has been reported using free nanoparticles (O'Neal et al., 209 Cancer Lett. 171 (2009)), the present embodiment is advantageous in that a tumor can be targeted and contacted directly with the photothermal element to effect subsequent ablation. Similarly, the conformal photothermal element can be used to fill a cavity, and then hardened by exposure to electromagnetic radiation. This method can be used to implant a bulking agent or tissue platform, or to form a depot for sustained/controlled release of an active agent.

In further aspects of the present invention, a silk fibroin-based photothermal element further comprises a thermoelectric device to form a photothermal-electric device. As used herein, the term "thermoelectric device" refers to a device converting a temperature difference to an electric voltage. The term "thermoelectric device" can also encompass a thermoelectric generator. In accordance with the invention, when the plasmonic nanoparticles of the photothermal element are exposed to electromagnetic radiation, a temperature difference is generated across a thermoelectric device, which can subsequently convert the temperature difference to voltage or electricity.

Accordingly, in some embodiments, the present invention provides a thermoelectric device comprising a nanoparticle-containing surface and a nanoparticle-free surface. The nanoparticle-containing surface of the device includes a photothermal element comprising a plurality of photothermal plasmonic nanoparticles distributed in a silk fibroin matrix. The nanoparticle-free surface of the device is substantially free of photothermal element, or contains significantly less photothermal element relative to the nanoparticle-containing surface, such that temperature differential may be established upon illumination with suitable light. In some embodiments, the nanoparticle-free surface of such a device comprises a plurality of nanoparticles that are sensitive to a discrete wavelength (or a range of wavelengths) of light such that heat generation by illumination can be differentially achieved on the two surfaces. Thus, illumination of the nanoparticle-containing surface of the device with suitable light causes light-activated heat generation on the surface, but not on the other surface with the particular light.

As a non-limiting example, a photothermal-electric element comprises a thermal power chip, the surface of which is coated with a plasmonic particle-doped silk fibroin matrix. A particular embodiment of such photothermal-electric element was produced by casting GNP-doped silk films on a commercially available thermal-power chip (1.6 mm×3.2 mm), that generated ~20 mW at ΔT of 60° C. using a continuous wave (CW) green laser with an output power up to 450 mW/mm$^2$ at 532 nm. In that embodiment, the GNPs can have a diameter of about 10 nm to about 20 nm.

In some embodiments, the silk fibroin matrix of the photothermal element of the invention has a thickness of at least twice the average diameter of the plasmonic nanoparticles. In some embodiments, the silk fibroin matrix of the photothermal element of the invention has a thickness of at least three time, four times, five times or more, the average diameter of the plasmonic nanoparticles.

The structure of described thermoelectric device comprising a nanoparticle-containing surface and a nanoparticle-free surface may be of substantially planar configuration, such as a chip, a film, a plate, a disc, etc. In some embodiments, one primary surface of such a structure constitutes a nanoparticle-containing surface, while the opposite side of the structure constitutes a nanoparticle-free surface. This may be achieved by coating or casting the first surface (but not the opposite surface) of the structure with a silk-based material (e.g., fibroin solution) mixed with plasmonic nanoparticles dispersed therein. This is schematically illustrated in FIG. 1. Upon drying the nanoparticle-doped silk material, the resulting structure comprises a nanoparticle-containing surface and a nanoparticle-free surface, such that when illuminated heat is generated on the first surface, creating temperature differentials across the thickness of the structure.

The size of the thermoelectric device can be selected for a particular application, for example, depending on the nature of the site of placement for the photothermal-electric device and/or the flexibility required therefor. Commercially available thermoelectric devices from an exemplary supplier range in size from about 0.35 mm to about 34.00 mm in length, from about 0.35 mm to about 2.40 mm in width, and from about 0.30 mm to about 5.00 mm in height, with an average electric conductivity value (for one batch) within range of about 850-1500 $Ohm^{-1}$ $cm^{-1}$ (Crystal Ltd. (Moscow, Russia; Align Sourcing LLC, Yardville, N.J., U.S.)). Thermoelectric devices have been produced with footprints between about 0.6 $mm^2$ and about 25 $mm^2$ (Micropelt GmbH, Freiburg, Germany); or from approximately 2.5-50 $mm^2$ and 2.5-5 mm in height (Ferro Tec, Santa Clara, Calif.); or from about 12 μm through about 32 μm, Kim et al., PowerMEMS 2009 281-284 (Washington, D.C., Dec. 1-4, 2009). Additionally, flexible thermoelectric devices have been designed. See Glatz et al., *Optimization and fabrication of thick flexible polymer based micro thermoelectric generator*, 132 Sensors & Actuators A 132 337 (2006); Glatz et al., $Bi_2Te_3$-based flexible micro thermoelectric generator with optimized design 18 J. Microeletromechanical Sys. 763 (2009).

Without wishing to be bound by theory, the photothermal-electric devices described herein can generate electricity via the Seebeck Effect, where electricity is produced from a temperature differential applied across the device. The temperature difference (ΔT) between the hot and the cold zones leads to change in the difference of the Fermi energies which yields a potential difference and drives a current. Accordingly, in some embodiments, the efficiency (P/ΔT and/or V/ΔT) can be improved at the expense of increasing the heating area. DiSalvo 285 Sci. 703 (1999). In some embodiments, the power requirements of the illumination source can be reduced by either increasing the concentration of the plasmonic nanoparticles, changing the composition of the plasmonic nanoparticles, or the thickness of the nanoparticle-doped silk film.

In some embodiments, the photothermal elements and/or the photothermo-electric devices described herein can further comprise a light source. In some embodiments, the light source can be provided by one or more light-emitting diodes (LEDs). In those embodiments, one or more LEDs can independently produce electromagnetic radiation, e.g., with a wavelength ranging from infra-red light, to visible light, to ultra-violet light. In some embodiments, the light source can be used to provide an electromagnetic radiation for the plasmonic nanoparticles described herein. In other instances, the light source can be activated by the heat or electricity generated by plasmonic nanoparticles, e.g., for diagnostic imaging.

Currently, inductive coils are one of the most popular elements used for wireless powering of IMDs. Soma et al., 34 IEEE Trans. Biomed. Engin. 276 (1987); Takeuchi & Shimoyama, A95 Sens. Actuators, A 269 (2002). The power transfer through inductive coupling between the implanted receiver coil and an outside source coil relies heavily on the coupling position/angle and drops rapidly with increased working distance. Fotopoulou & Flynn, in 2006 5th IEEE Conf. Sensors 765 (2007). Photothermal-electric powering approaches have looser requirements on the separation between the patient and the illumination source, which could be useful in a surgical setting where spatial constraints are paramount. Additionally, this approach can avoid the issues of magnetic field exposure and device interference, which have recently become of increased concern for IMDs for reasons of safety and privacy. Maisel & Kohno, 362 N. Engl. J. Med. 1164 (2010).

Silk matrices comprising plasmonic nanoparticles constitute a promising building block for silk based bio-implantable and resorbable devices. In some embodiments, integrating thermoelectric functionality with silicon electronics, and/or other working components such as n-channel metal-oxide-semiconductor (nMOS) transistors (Kim et al., 95 Appl. Phys. Lett. 133701 (2009)), and passive neural recording electrodes (Kim et al., 9 Nature Mats. 511 (2010)), can expand the utility of such devices in various biomedical applications.

In some embodiments, the devices of the present invention can take advantage of the many techniques developed to functionalize silk fibroin matrix for various applications, such as drug delivery, biosensing, and optical imaging. See, e.g., U.S. Pat. No. 6,287,340, Bioengineered anterior cruciate ligament; WO 2004/000915, Silk Biomaterials & Methods of Use Thereof; WO 2004/001103, Silk Biomaterials & Methods of Use Thereof; WO 2004/062697, Silk Fibroin Materials & Use Thereof; WO 2005/000483, Method for Forming inorganic Coatings; WO 2005/012606, Concentrated Aqueous Silk Fibroin Solution & Use Thereof; WO 2011/005381, Vortex-Induced Silk fibroin Gelation for Encapsulation & Delivery; WO 2005/123114, Silk-Based Drug Delivery System; WO 2006/076711, Fibrous Protein Fusions & Uses Thereof in the Formation of Advanced Organic/Inorganic Composite Materials; U.S. Application Pub. No. 2007/0212730, Covalently immobilized protein gradients in three-dimensional porous scaffolds; WO 2006/042287, Method for Producing Biomaterial Scaffolds; WO 2007/016524, Method for Stepwise Deposition of Silk Fibroin Coatings; WO 2008/085904, Biodegradable Electronic Devices; WO 2008/118133, Silk Microspheres for Encapsulation & Controlled Release; WO 2008/108838, Microfluidic Devices & Methods for Fabricating Same; WO 2008/127404, Nanopatterned Biopolymer Device & Method of Manufacturing Same; WO 2008/118211, Biopolymer Photonic Crystals & Method of Manufacturing Same; WO 2008/127402, Biopolymer Sensor & Method of Manufacturing Same; WO 2008/127403, Biopolymer Optofluidic Device & Method of Manufacturing the Same; WO 2008/127401, Biopolymer Optical Wave Guide & Method of Manufacturing Same; WO 2008/140562, Biopolymer Sensor & Method of Manufacturing Same; WO 2008/127405, Microfluidic Device with Cylindrical Microchannel & Method for Fabricating Same; WO 2008/106485, Tissue-Engineered Silk Organs; WO 2008/140562, Electroactive Biopolymer Optical & Electro-Optical Devices & Method of Manufacturing Same; WO 2008/150861, Method for Silk Fibroin Gelation Using Sonication; WO 2007/103442, Biocompatible Scaffolds & Adipose-Derived Stem Cells; WO 2009/155397, Edible Holographic Silk Products; WO 2009/100280, 3-Dimensional Silk Hydroxyapatite Compositions; WO 2009/061823, Fabrication of Silk Fibroin Photonic Structures by Nanocontact Imprinting; WO 2009/126689, System & Method for Making Biomaterial Structures.

In some embodiments, the photothermal or photothermal-electric elements of the present invention can also be used as sensors, or can include sensors, for use in biological or other environments. See, e.g., WO 2010/126640, Nanoimprinting of Silk Fibroin Structures for Biomedical & Biophotonic Applications; WO 2008/127401; WO 2008/118211; WO 2008/127402; WO 2008/140562. The silk fibroin-based photothermal or photothermal-electric elements of the present invention can also be combined with other silk fibroin-based photonic structures, including silk fibroin-based holograms and silk fibroin-based optical fibers. See, e.g., WO 2009/061823; PCT/US10/50565, Drawn Silk E-Gel Fibers & Methods of Making Same; PCT/US2010/042585, All-Protein Implantable, Resorbable Reflectors; PCT/US10/47307, Silk Transistor Devices & Method of Making Transistor Devices from Silk.

As mentioned above, it is contemplated that plasmonic nanoparticle-doped silk fibroin matrix described herein can be used for in vivo photothermal therapy. Without wishing to be bound by theory, since the plasmonic nanoparticle-doped silk fibroin matrix can be adapted to conform to the treated area, it can increase the efficiency of heat transfer to the target area or tissue, and/or be placed over a curved surface. For example, the photothermal element can be inserted at the joint, where heat generated by the photothermal element can relieve joint pain, e.g., arthritis pain. See, e.g., Jaeger et al., 49 Acta Vet. Scanda. (2007). Additionally, the plasmonic nanoparticle-doped silk films can be used for in vivo to generate power (in combination with an appropriate thermoelectric device) during treatment for on-site data recording and transmitting devices. In use, electromagnetic radiation can be transmitted in a pattern, such that predetermined specific areas of the photothermal element or the photothermal-electric device can be irradiated to convert the optical activation to heat or electricity. Additionally, light of a predetermined frequency (e.g., color, diffraction gradient) can be used to control the amount of heat or electricity generated by the photothermal element or photothermal-electric device.

In another embodiment, the photothermal-electric device can comprise piezoelectric silk fibroin material, i.e., a silk fibroin material that can generate electricity under an applied mechanical force, and/or deformation of the silk fibroin material, and vice versa. See WO 2010/036992, Active Silk Muco-Adhesives, Silk Electrogelation Process & Devices; U.S. Ser. No. 12/974,796, pH-Induced Silk Gels & Uses Thereof. The ability to regulate conformation of silk fibroin proteins via irradiation is useful for, e.g., effecting active agent release from the silk fibroin matrix or altering the degradation rate of the silk fibroin matrix as desired.

Another embodiment provides for a method of generating electricity comprising (a) providing a photothermal element comprising a silk fibroin matrix comprising plasmonic nanoparticles that absorb incident radiation to generate heat when irradiated with electromagnetic radiation, and a thermoelectric device in thermal contact with the photothermal element, wherein the thermoelectric device converts the heat transferred from the photothermal element into electricity; b) irradiating the photothermal element with electromagnetic radiation; wherein the thermoelectric device converts the heat transferred from the photothermal element into electricity. In some embodiments, the irradiating can be applied through a catheter-based optical fiber, which can include a silk optical fiber. In some embodiments, the electromagnetic radiation can be near infrared electromagnetic radiation.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

EXAMPLES

Example 1

Preparation of Gold Nanoparticle (GNP)-Doped Silk Fibroin

Production of the silk fibroin solution and synthesis of GNP has been described previously in the literature. Sofia et al., 54 J. Biomed. Mats. Res. 139 (2001); Kimling et al., 110 J. Phys. Chem. B. 15700 (2006). Briefly, *Bombyx mori* cocoons are cut into small pieces and boiled in a 0.02 M aqueous solution of sodium carbonate ($Na_2CO_3$) for 60 min to remove sericin, a water-soluble glycoprotein which binds fibroin filaments (FIGS. 1a and 1b). The resulting fibroin bundle is dried and then dissolved in a 9.3 M aqueous solution of lithium bromide (LiBr) at 60° C. for 12 hr (FIG. 1c). The lithium bromide salt is then extracted through a water-based dialysis process (FIG. 1d). It is essential to make an ion-free silk solution to achieve uniform mixing with the GNPs. The resulting solution is then centrifuged and filtered via syringe-based micro-filtration (5 μm pore size, Millipore Inc., Medford, Mass.) to remove any residual particulates, producing 8% w/v silk fibroin solution with minimal contaminants. The GNP solution is prepared by adding 20 mL 1% trisodium citrate ($Na_3C_6H_5O_7$) into 200 mL boiled 1.0 mM hydrogen tetrachloroaurate ($HAuCl_4$), followed by continuously heating for 10 min or until the solution has turned deep red. After production of the silk fibroin and GNP solution, the GNP solution is carefully added into the silk solution and gentle agitation is applied to get uniform dispersion (FIG. 1e).

A series of silk-GNP samples, with different GNP concentrations diluted by de-ionized water, were prepared and characterized for light absorption responses using UV-Vis spectrometer (HP 8452A, Hewlett-Packard Company) at wavelengths ranging from 350 nm to 750 nm, with a resolution of 1 nm. As shown in FIG. 2, GNP-doped silk samples show a noticeable absorption peak at ~530 nm. Silk solution with a higher GNP concentration shows higher peak absorbance while the undoped sample shows a non-resonant absorption response in the visible frequency range, which can be also verified visually by observing the color difference.

Example 2

Preparation of a Photothermal-Electric Device Comprising a GNP-Doped Silk Fibroin Film Eight (8) μL, of the silk GNP solution was cast on the top side (hot zone) of a commercially purchased thermo-electric chip (ETEG UPF40, Nextreme Thermal Solutions, Inc., Durham, N.C.), and allowed to set for 2 hr, resulting in approximately 30 μm thick film (FIGS. 1f and 1g). An interface testing circuit to monitor the temperature increase and power output is used for characterization of the GNP-doped silk fibroin film photothermal-electric device (FIG. 1h).

A CW green laser was used to illuminate the silk-GNP coated photothermal-electric chip, and two thermocouples attached to the hot and cold zones of the chip monitored the temperature difference induced by the silk film with embedded GNPs upon illumination. As shown in FIG. 3, the open circuit voltage (V) increases to 160 mV at a ΔT of 60° C. when the laser output power is set to 1.15 W, namely 450 $mW/mm^2$ and for a laser spot size of ~1.8 mm in diameter. This provides a maximum generated power (P) of 20 mW under a load resistance R=0.3Ω. For implantable device applications, power generation performance with small temperature differentials is essential to avoid tissue damage. Lowering the incident laser power to 50 mW causes a temperature increase of 1.3° C. which generates a maximum voltage of 7.4 mV and peak power of 70 μW. These values are within the operating range of existing low power IMDs such as pacemakers (<10 μW) (Chandrakasan et al., 10 Ann. Rev. Biomed. Engin. 247 (2008)), or complementary metal-oxide semiconductor (CMOS) amplifiers for neural signal acquisition (~60 μW) (Li & Tang, in Proc. 31th Ann. Intl. Conf. IEEE Engin. Med. & Bio. Socy. 3806 (2009)). The photothermal-electric device used in this Example generates electricity via the Seebeck Effect, where electricity is produced from a temperature differential applied across the device. The temperature difference (ΔT) between the hot and the cold zones leads to change in the difference of the Fermi energies which yields a potential difference and drives a current. Therefore the efficiency (P/ΔT and/or V/ΔT) can be potentially improved at the expense of increasing the heating area. DiSalvo 285 Sci. 703 (1999). Additionally, the power requirements of the illumination source can be reduced by either increasing the concentration of the GNPs or the thickness of the GNP doped silk film.

We claim:

1. A photothermal element comprising:
a plurality of plasmonic nanoparticles that generate heat when exposed to electromagnetic radiation; and
a silk fibroin matrix,
wherein the plurality of plasmonic nanoparticles is distributed within the silk fibroin matrix; and,
wherein the average diameter of the plurality of plasmonic nanoparticles is between about 5 nm and 100 nm.

2. The photothermal element of claim 1, wherein the silk fibroin matrix is in a form of:
a wire, an optical fiber, a film, an ultrathin film, a gel, an injectable matrix, a coating, a vesicle, a sponge, a block, a porous structure or any combination thereof.

3. The photothermal element of claim 1 wherein the silk fibroin matrix has a thickness of 30 nm to 500 μm.

4. The photothermal element of claim 1, wherein the photothermal element is adapted to conform to a surface upon contact with the surface.

5. The photothermal element of claim 1, wherein the plurality of plasmonic nanoparticles are evenly dispersed within the silk fibroin matrix.

6. The photothermal element of claim 1, wherein the plurality of plasmonic nanoparticles are distributed in a gradient within the silk fibroin matrix.

7. The photothermal element of claim 1, wherein the plurality of plasmonic nanoparticles are distributed in a pattern, said pattern comprises an optical pattern, a micropattern, or a nanopattern.

8. The photothermal element of claim 1, wherein the at least one plasmonic nanoparticle is selected from the group consisting of a nanosphere, a nanoshell, a nanorod, a nanocage, a nanocrystal, nanopowder, and any combinations thereof.

9. The photothermal element of claim 1, wherein the plurality of plasmonic nanoparticles comprise at least one metal.

10. The photothermal element of claim 9, wherein the metal is selected from the group consisting of a noble metal, a non-noble metal, an oxide thereof, an alloy thereof, and any combinations thereof.

11. The photothermal element of claim 10, wherein the noble metal is gold.

12. The photothermal element of claim 1, further comprising a thermo-electric device.

13. The photothermal element of claim 1, wherein the plurality of plasmonic nanoparticles and/or the silk fibroin matrix further comprises at least one active agent.

14. The photothermal element of claim 1, further comprising at least one contrast-enhancing agent.

15. The photothermal element of claim 1, wherein the silk fibroin matrix further comprises at least one optical pattern to modulate the electromagnetic radiation.

16. An implantable device comprising the photothermal element of claim 1, wherein the implantable device is configured for in vivo photothermal therapy.

17. A photothermal-electric device comprising:
a photothermal element of claim 1; and
a thermoelectric device in contact with the photothermal element, wherein the thermoelectric device converts at least a portion of heat transferred from the photothermal element into electricity.

18. The photothermal-electric device of claim 17, further comprising an electric circuit connected to the thermoelectric device to transmit the converted electricity as an output energy.

19. The photothermal-electric device of claim 17, wherein the thermoelectric device comprises a thin-film thermoelectric material.

20. The photothermal-electric device of claim 17, wherein the thermoelectric device is adapted to conform to a surface upon contact with the surface.

21. A wireless powering device comprising the photothermal-electric device of claim 17.

22. The wireless powering device of claim 21 wherein the wireless powering device is adapted to conform to a surface upon contact with the surface.

23. The wireless powering device of claim 21, wherein the wireless powering device is adapted to be implantable.

24. A method of photothermal therapy comprising:
(a) contacting an internal or external tissue with a silk fibroin-based photothermal element comprising a silk fibroin matrix and a plurality of plasmonic nanoparticles dispersed therein, wherein the silk fibroin-based photothermal element is adapted to conform to the tissue upon contact; and
(b) exposing the at least one plasmonic nanoparticle to electromagnetic radiation, wherein the at least one plasmonic nanoparticle generates heat upon irradiation, and wherein at least a portion of the generated heat is transferred to at least a portion of the tissue.

25. The method of claim 24, wherein the silk fibroin-based photothermal element comprises at least one active agent.

26. The method of claim 24, further comprising modulating the electromagnetic radiation,
wherein the modulation of the electromagnetic radiation is selected from the group consisting of:
modulating the intensity of a source of the electromagnetic radiation;
modulating the distribution of the source of the electromagnetic radiation;
applying at least one optical grating to the source of the electromagnetic radiation;
varying the wavelength of the electromagnetic radiation; and
any combinations thereof.

27. The method of claim 26, wherein the at least one optical grating is adapted to localize the heat generation.

28. A method of generating electricity comprising:
(a) providing a photothermal element comprising a silk fibroin matrix, the silk fibroin matrix comprising at least one plasmonic nanoparticle that absorbs radiation to generate heat when irradiated with electromagnetic radiation, and a thermoelectric device in contact with the photothermal element;
(b) irradiating the photothermal element with electromagnetic radiation, wherein the thermoelectric device converts at least a portion of the heat transferred from the photothermal element into electricity.

29. The method of claim 28, further comprising modulating the electromagnetic radiation,
wherein the modulation of the electromagnetic radiation is selected from the group consisting of:
modulating the intensity of a source of the electromagnetic radiation;
modulating the distribution of the source of the electromagnetic radiation;
applying at least one optical grating to the source of the electromagnetic radiation;
varying the wavelength of the electromagnetic radiation; and
any combinations thereof.

30. The method of claim 28, wherein the method is adapted for an in vivo application.

31. The method of claim 28, further comprising connecting the thermoelectric device with an electric circuit to transmit at least a portion of the generated electricity as an output energy.

* * * * *

UNITED STATES PATENT AND TRADEMARK OFFICE
CERTIFICATE OF CORRECTION

PATENT NO.        : 9,517,357 B2
APPLICATION NO.   : 13/819419
DATED             : December 13, 2016
INVENTOR(S)       : Omenetto et al.

It is certified that error appears in the above-identified patent and that said Letters Patent is hereby corrected as shown below:

In the Claims

Please correct Claim 8 from:
"The photothermal element of claim 1, wherein the at least one plasmonic nanoparticle is selected from the group consisting of a nanosphere, a nanoshell, a nanorod, a nanocage, a nanocrystal, nanopowder, and any combinations thereof"

To read:
-- The photothermal element of claim 1, wherein the plurality of plasmonic nanoparticles is selected from the group consisting of a nanosphere, a nanoshell, a nanorod, a nanocage, a nanocrystal, nanopowder, and any combinations thereof. --

Signed and Sealed this
Ninth Day of May, 2017

Michelle K. Lee
*Director of the United States Patent and Trademark Office*